(12) United States Patent
Harlev et al.

(10) Patent No.: US 8,137,343 B2
(45) Date of Patent: Mar. 20, 2012

(54) TRACKING SYSTEM USING FIELD MAPPING

(75) Inventors: Doron Harlev, Cambridge, MA (US); Rotem Eldar, Cambridge, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 633 days.

(21) Appl. No.: 12/258,677

(22) Filed: Oct. 27, 2008

(65) Prior Publication Data
US 2010/0106154 A1   Apr. 29, 2010

(51) Int. Cl.
   *A61B 18/18*   (2006.01)
(52) U.S. Cl. ............... 606/41; 600/508; 600/509
(58) Field of Classification Search .......... 600/509; 607/115, 119, 122, 127; 606/41
   See application file for complete search history.

(56) References Cited

U.S. PATENT DOCUMENTS

| | | | |
|---|---|---|---|
| 4,649,924 A | 3/1987 | Taccardi | 128/642 |
| 4,674,518 A | 6/1987 | Salo | 128/695 |
| 4,840,182 A | 6/1989 | Carlson | 128/694 |
| 4,920,490 A | 4/1990 | Isaacson | 364/413.13 |
| 5,156,151 A | 10/1992 | Imran | |
| 5,284,142 A | 2/1994 | Goble et al. | 128/653.1 |
| 5,297,549 A | 3/1994 | Beatty et al. | 128/642 |
| 5,300,068 A | 4/1994 | Rosar et al. | |
| 5,341,807 A | 8/1994 | Nardella | 128/642 |
| 5,381,333 A | 1/1995 | Isaacson et al. | 364/413.13 |
| 5,480,422 A | 1/1996 | Ben-haim | 607/122 |
| 5,500,011 A | 3/1996 | Desai | 607/116 |
| 5,553,611 A | 9/1996 | Budd et al. | 128/642 |
| 5,568,809 A | 10/1996 | Ben-Haim | 128/656 |
| 5,577,502 A | 11/1996 | Darrow et al. | 128/653.1 |
| 5,662,108 A | 9/1997 | Budd et al. | 128/642 |
| 5,687,737 A | 11/1997 | Branham et al. | 128/710 |
| 5,697,377 A | 12/1997 | Wittkampf | 128/696 |
| 5,704,365 A | 1/1998 | Albrecht et al. | |
| 5,722,402 A | 3/1998 | Swanson et al. | 128/642 |
| 5,846,198 A | 12/1998 | Killmann | |
| 5,848,972 A | 12/1998 | Triedman et al. | |
| 5,921,982 A | 7/1999 | Lesh et al. | |
| 5,971,933 A | 10/1999 | Gopakumaran et al. | 600/526 |
| 5,983,126 A | 11/1999 | Wittkampf | |
| 6,050,267 A | 4/2000 | Nardella et al. | 128/899 |
| 6,095,150 A | 8/2000 | Panescu et al. | 128/899 |

(Continued)

OTHER PUBLICATIONS

Notification of Transmittal of the International Search Report and the Written Opinion of the International Searching Authority, or the Declaration, International Application No. PCT/US2009/061277, Apr. 8, 2010, 13 pages.

(Continued)

*Primary Examiner* — Laura Bouchelle
(74) *Attorney, Agent, or Firm* — Fish & Richardson P.C.

(57) ABSTRACT

In some aspects, a method includes (i) securing multiple sets of current injecting electrodes to an organ in a patient's body, (ii) causing current to flow among the multiple sets of current injecting electrodes to generate a field in the organ, (iii) in response to current flow caused by the multiple sets of current injecting electrodes, measuring the field at each of one or more additional electrodes, (iv) determining expected signal measurements of the field inside the organ using a pre-determined model of the field, and (v) determining a position of each of the one or more additional electrodes in the organ based on the measurements made by the additional electrodes and the determined expected signal measurements of the field.

69 Claims, 10 Drawing Sheets

U.S. PATENT DOCUMENTS

| | | | |
|---|---|---|---|
| 6,167,296 A | 12/2000 | Shahidi | |
| 6,240,307 B1 | 5/2001 | Beatty et al. | 600/374 |
| 6,246,898 B1 | 6/2001 | Vesely et al. | |
| 6,254,536 B1 | 7/2001 | DeVito | 600/300 |
| 6,278,894 B1 | 8/2001 | Salo et al. | 600/547 |
| 6,298,257 B1 | 10/2001 | Hall et al. | |
| 6,308,093 B1 | 10/2001 | Armoundas et al. | 600/509 |
| 6,314,310 B1 | 11/2001 | Ben-Haim et al. | |
| 6,317,619 B1 | 11/2001 | Boernert et al. | |
| 6,318,375 B1 | 11/2001 | Plicchi et al. | 128/899 |
| 6,360,123 B1 | 3/2002 | Kimchi et al. | 600/547 |
| 6,368,285 B1 | 4/2002 | Osadchy et al. | 600/508 |
| 6,400,981 B1 | 6/2002 | Govari | 600/509 |
| 6,516,807 B1 | 2/2003 | Panescu et al. | |
| 6,547,082 B1 | 4/2003 | Babini | 211/41.17 |
| 6,556,695 B1 | 4/2003 | Packer et al. | 382/128 |
| 6,574,492 B1 | 6/2003 | Ben-Haim et al. | |
| 6,574,498 B1 | 6/2003 | Gilboa | 600/424 |
| 6,593,884 B1 | 7/2003 | Gilboa et al. | 342/448 |
| 6,600,948 B2 | 7/2003 | Ben-Haim et al. | |
| 6,603,996 B1 | 8/2003 | Beatty et al. | 600/513 |
| 6,640,119 B1 | 10/2003 | Budd et al. | 600/374 |
| 6,650,927 B1 | 11/2003 | Keidar | 600/424 |
| 6,690,963 B2 | 2/2004 | Ben-haim et al. | 600/424 |
| 6,701,176 B1 | 3/2004 | Halperin et al. | 600/411 |
| 6,728,562 B1 * | 4/2004 | Budd et al. | 600/374 |
| 6,773,402 B2 | 8/2004 | Govari et al. | |
| 6,807,439 B2 | 10/2004 | Edwards et al. | 600/420 |
| 6,839,588 B1 | 1/2005 | Rudy | 600/523 |
| 6,847,839 B2 | 1/2005 | Ciaccio et al. | |
| 6,872,428 B2 | 3/2005 | Yang et al. | 427/568 |
| 6,892,090 B2 | 5/2005 | Verard et al. | |
| 6,892,091 B1 | 5/2005 | Ben-Haim et al. | |
| 6,939,309 B1 | 9/2005 | Beatty et al. | 600/508 |
| 6,978,168 B2 | 12/2005 | Beatty et al. | 600/513 |
| 6,990,370 B1 | 1/2006 | Beatty et al. | 600/509 |
| 7,016,719 B2 | 3/2006 | Rudy et al. | |
| 7,043,292 B2 * | 5/2006 | Tarjan et al. | 600/509 |
| 7,263,397 B2 | 8/2007 | Hauck et al. | 600/374 |
| 2003/0018251 A1 | 1/2003 | Solomon | 600/427 |
| 2003/0065271 A1 | 4/2003 | Khoury | 600/509 |
| 2003/0076277 A1 | 4/2003 | Muramatsu et al. | 345/1.1 |
| 2004/0077942 A1 | 4/2004 | Hall et al. | 600/428 |
| 2004/0097806 A1 | 5/2004 | Hunter et al. | 600/434 |
| 2004/0254437 A1 | 12/2004 | Hauck et al. | 600/374 |
| 2005/0038337 A1 | 2/2005 | Edwards | 600/424 |
| 2005/0054918 A1 | 3/2005 | Sra | 600/427 |
| 2005/0154282 A1 | 7/2005 | Li et al. | 600/407 |
| 2005/0288599 A1 | 12/2005 | MacAdam et al. | |
| 2006/0085049 A1 | 4/2006 | Cory et al. | 607/48 |
| 2006/0116575 A1 | 6/2006 | Willis | 600/434 |
| 2006/0122526 A1 | 6/2006 | Berenfeld et al. | |
| 2006/0173251 A1 | 8/2006 | Govari et al. | 600/306 |
| 2006/0241401 A1 | 10/2006 | Govari et al. | 600/424 |
| 2007/0016007 A1 | 1/2007 | Govari et al. | 600/424 |
| 2007/0038078 A1 * | 2/2007 | Osadchy | 600/424 |
| 2007/0299351 A1 | 12/2007 | Harlev et al. | 600/509 |
| 2007/0299352 A1 * | 12/2007 | Harlev et al. | 600/509 |
| 2008/0234588 A1 * | 9/2008 | Feldman et al. | 600/486 |

OTHER PUBLICATIONS

Notification of Transmittal of the International Search Report and the Written Opinion of the International Searching Authority, or the Declaration, PCT/US2009/036099, Dated Apr. 28, 2009, 21 pages.

Adams et al., "Seeded Region Growing", *IEEE Transactions on Pattern Analysis and Machine Intelligence*, 16(6):641-647, 1994.

Baan, Jan et al., "Continuous Measurement of Left Ventricular Volume In Animals and Humans by Conductance Catheter", Circulation, vol. 70, pp. 812-823.

Ben-Haim et al., "Nonfluoroscopic, in Vivo Navigation and Mapping Technology", *Nature Medicine*, 2(12):1393-1395, 1996.

Besl et al., "A Method for Registration of 3-D Shapes", *IEEE Transactions on Pattern Analysis and Machine Intelligence*, 14(2):239-256, 1992.

Blomström-Lundqvist et al., "ACC/AHA/ESC Guidelines for the Management of Patients With Supraventricular Arrhythmias-Executive Summary", *Journal of the American College of Cardiology*, 42(8):1493-1531, 2003.

Breithardt et al., "AHA Medical/Scientific Statement—Special Report: Standards for Analysis of Ventricular Late Potentials Using High-Resolution or Signal-Averaged Electrocardiography", *Circulation*, 83(4):1481-1488, 1991.

Brooks et al., "Electrical Imaging of the Heart", *IEEE Signal Processing Magazine*, pp. 24-42, 1997.

Caspi et al., "Stem Cell Research: Regenerating the Heart Using Human Embryonic Stem Cells—from Cell to Bedside", *IMAJ*, 8:208-214, 2006.

De Groot et al., "Three-Dimensional Catheter Positioning During Radiofrequency Ablation in Patients: First Application of a Real-Time Position Management System", *Journal of Cardiovascular Electrophysiology*, 11:1183-1192, 2000.

Donahue et al., "Focal Modification of Electrical Conduction in the Heart by Viral Gene Transfer", *Nature Medicine*, 6(12):1395-1398, 2000.

Dong et al., "Integrated Electroanatomic Mapping With Three-Dimensional Computed Tomographic Images for Real-Time Guided Ablations", *Circulation*, 113:186-194, 2006.

Durrer et al., "Total Excitation of the Isolated Human Heart", *Circulation*, vol. XLI, pp. 899-912, 1970.

Ector, Joris et al., "Cardiac Three-Dimensional Magnetic Resonance Imaging and Fluoroscopy Merging", Circulation, (Dec. 13, 2005).

Friedman, "Catheter Cryoablation of Cardiac Arrhythmias", *Current Opinion in Cardiology*, 20:48-54, 2005.

Friedman, "Novel Mapping Techniques for Cardiac Electrophysiology", *Heart*, 87:575-582, 2002.

Geddes, L.A. et al., "Criteria for the Selection of Materials for Implanted Electrodes", Annals of Biomedical Engineering, vol. 31, pp. 879-890 (2003).

Gepstein et al., "A Novel Method for Nonfluoroscopic Catheter-Based Electroanatomical Mapping of the Heart", *Circulation* 95:1611-1622, 1997.

Huang, Yi-Chih et al., "Development of a Third Generation Intraventricular Impedance Imaging (Iii) System Evaluation of Hardware Design", Engineering in Medicine and Biology Society,. Proceedings of the 19th Annual International Conference of the IEEE, Oct. 30-Nov. 2, 1997 vol. 6, (1997).

Jain et al., "Cell Therapy Attenuates Deleterious Ventricular Remodeling and Improves Cardiac Performance After Myocardial Infarction", *Circulation*, 103:1920-1927, 2001.

Jalife, "Rotors and Spiral Waves in Atrial Fibrillation", *Journal of Cardiovascular Electrophysiology*, 14:776-780, 2003.

Jané et al., "Alignment Methods for Averaging of High-Resolution Cardiac Signals: A Comparative Study of Performance", *IEEE Transactions on Biomedical Engineering*, 38(6):571-579, 1991.

Jia et al., "Electrophysiologic Endocardial Mapping From a Noncontact Nonexpandable Catheter: A Validation Study of a Geometry-Based Concept", *Journal of Cardiovascular Electrophysiology*, 11:1238-1251, 2000.

Kikuchi et al., "Targeted Modification of Atrial Electrophysiology by Homogeneous Transmural Atrial Gene Transfer", *Circulation*, 111:264-270, 2005.

Kistler et al., "Validation of Three-Dimensional Cardiac Image Integration: Use of Integrated CT Image into Electroanatomic Mapping System to Perform a Catheter Ablation of Atrial Fibrillation", *Journal of Cardiovascular Electrophysiology*, 17:341-348, 2006.

Kun, Stevan et al., "Conductance Volumetric Model of an Eccentrically Positioned Catheter Within a Three-Compartment Ellipsoidal Ventricle", U, IEEE Transactions on, Jun. 1993, vol. 40, Issue: 6.

Laciar et al., "Improved Alignment Method for Noisy High-Resolution ECG and Holter Records Using Multiscale Cross-Correlation", *IEEE Transactions on Biomedical Engineering*, 50(3):344-353, 2003.

Liu et al., "Endocardial Potential Mapping From a Noncontact Nonexpandable Catheter: A Feasibility Study", *Annals of Biomedical Engineering*, 26:994-1009, 1998.

Lorensen et al. "Marching Cubes: A High Resolution 3D Surface Construction Algorithm". *Computer Graphics* 21(4):163-169, Jul. 1987.

Mäkelä et al., "A Review of Cardiac Image Registration Methods", *IEEE Transactions on Medical Imaging*, 21(9):1011-1021, 2002.

Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252, (1996).

Mangan, Alan et al., "Partitioning 3D Surface Meshes Using Watershed Segmentation", IEEE Transactions on Visualization and Computer Graphics, vol. 05, No. 4, pp. 308-321, (Oct.-Dec. 1999).

Meininger et al., "Initial Experience with a Novel Focused Ultrasound Ablation System for Ring Ablation Outside the Pulmonary Vein", *Journal of Interventional Cardiac Electrophysiology*, 8:141-148, 2003.

Merrill, Daniel R. et al., "Electrical stimulation of excitable tissue: design of efficacious and safe protocols", Journal of Neuroscience Methods, vol. 141, pp. 171-198 (2005).

Miller, "Editor's Forum—Application of Registration for Ablation: A Marriage of Technologies", *Journal of Interventional Cardiac Electrophysiology*, 11:87-89, 2004.

Nademanee et al., "A New Approach for Catheter Ablation of Atrial Fibrillation: Mapping of the Electrophysiologic Substrate", *Journal of the American College of Cardiology*, 43(11):2044-2053, 2004.

Noseworthy et al., "The Impact of Respiration on Left Atrial and Pulmonary Venous Anatomy: Implications for Image-Guided Intervention", *Heart Rhythm*, 2:1173-1178, 2005.

Pappone et al., "Robotic Magnetic Navigation for Atrial Fibrillation Ablation", *Journal of the American College of Cardiology*, 47(7):1390-1400, 2006.

Paragios, "A Level Set Approach for Shape-Driven Segmentation and Tracking of the Left Ventricle", *IEEE Transactions on Medical Imaging*, 22(6):773-776, 2003.

Persson et al., "A Simple Mesh Generator in MATLAB", *SIAM Review*, 46(2):329-345, 2004.

Persson, "Mesh Generation for Implicit Geometries", *Massachusetts Institute of Technology—Thesis*, Feb. 5, 2006.

Pham, Dzung et al., "Current Methods in Medical Image Segmentation", Annu. Rev. Biomed. Eng., 02: pp. 315-337, (2000).

Rao et al., "Novel Noncontact Catheter System for Endocardial Electrical and Anatomical Imaging", *Annals of Biomedical Engineering*, 32(4):573-584, 2004.

Reddy et al., "Integration of Cardiac Magnetic Resonance Imaging With Three-Dimensional Electroanatomic Mapping to Guide Left Ventricular Catheter Manipulation—Feasibility in a Porcine Model of Healed Myocardial Infarction", *Journal of the American College of Cardiology*, 44(11):2202-2213, 2004.

Reddy et al., "Use of a Diode Laser Balloon Ablation Catheter to Generate Circumferential Pulmonary Venous Lesions in an Open-Thoracotomy Caprine Model", *PACE*, 27:52-57, 2004.

Sanders et al., "Spectral Analysis Identifies Sites of High-Frequency Activity Maintaining Atrial Fibrillation in Humans", *Circulation*, 112:789-797, 2005.

Sethian. "Level Set Methods and Fast Marching Methods: Evolving Interfaces in Computational Geometry, Fluid Mechanics, Computer Vision, and Materials Science". *Department of Mathematics-University of California, Berkeley*. Cambridge University Press, 1999.

Simon et al., "Electroanatomic Mapping of the Right Atrium With a Right Atrial Basket Catheter and Three-Dimensional Intracardiac Echocardiography", *PACE*, 27:318-326, 2004.

Smits et al., "Catheter-Based Intramyocarial Injection of Autologous Skeletal Myoblasts as a Primary Treatment of Ischemic Heart Failure", *Journal of the American College of Cardiology*, 42(12):2063-2069, 2003.

Solomon et al., "Real-Time Cardiac Catheter Navigation on Three-Dimensional CT Images", *Journal of Interventional Cardiac Electrophysiology*, 8:27-36, 2003.

Sra, Jasbir et al, "Registration of 3D Computed Tomographic Images With Interventional Systems: Implications for Catheter Ablation of Atrial Fibrillation", J Interv Card Electrophysiol, 16: pp. 141-148, (2006).

Sra et al., "Registration of Three-Dimensional Left Atrial Computed Tomographic Images With Projection Images Obtained Using Fluoroscopy", *Circulation*, 112:3763-3768, 2005.

Stevenson, "Radiofrequency Catheter Ablation of Ventricular Tachycardia After Myocardial Infarction", *Circulation*, 98:308-314, 1998.

Taccardi et al., "A New Intracavitary Probe for Detecting the Site of the Origin of Ectopic Ventricular Beats During One Cardiac Cycle", *Circulation*, 75(1):272-281, 1987.

Thal et al., "Novel Applications in Catheter Ablation", *Journal of Interventional Cardiac Electrophysiology*, 13:17-21, 2005.

Thiagalingam et al., "Noncontact Mapping of the Left Ventricle: Insights from Validation With Transmural Contact Mapping", *PACE*, 27:570-578, 2004.

Voth, "The Inverse Problem of Electrocardiography: Industrial Solutions and Simulations", BEM and NFSI Conference Proceedings, Minneapolis, MN, May 12-15, 2005, pp. 191-194.

Wittkampf et al., "LocaLisa: New Technique for Real-Time 3-Dimensional Localization of Regular Intracardiac Electrodes", *Circulation*, 99:1312-1317, 1999.

Yezzi, Anthony et al., "A Geometric Snake Model for Segmentation", IEEE Transactions on Medical Imaging, vol. 16, No. 2, (Apr. 1997).

International Search Report and the Written Opinion, PCT/US07/70854, Sep. 12, 2008, 15 pages.

International Search Report and he Written Opinion, PCT/US08/52385, Aug. 8, 2008, 11 pages.

Authorized officer Nora Lindner, International Preliminary Report on Patentability in PCT/US2009/061277 mailed May 12, 2011, 12 pages.

* cited by examiner

TRACKING SYSTEM USING FIELD MAPPING

TECHNICAL FIELD

This invention relates to determining the position of an object, such as tracking the position of one or more catheters in a patient's heart cavity.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Under some circumstances, the location of the catheter in the heart chamber is determined using a tracking system. Catheter tracking is a core functionality of modern mapping systems that also include software and graphic user interface to project electrical data on 3D renderings of cardiac chambers. Currently there are several tracking systems available, some more useful and commonly used than others. Some systems are based on the use of magnetic or electric fields from external sources to sense and track the location of the catheter. Some are based on the use of magnetic or electric fields sources mounted on the tracked catheters.

SUMMARY

In some aspects, a method includes (i) causing current to flow among multiple sets of current injecting electrodes to generate a field in an organ, (ii) obtaining the positions of one or more measuring electrodes used for measuring the field generated by the current injecting electrodes, (iii) in response to the current flow, measuring the field at multiple locations in the organ using the one or more measuring electrodes, (iv) modeling the field using the measurements of the field from the one or more measuring electrodes and the positions of the one or more measuring electrodes, and (v) determining expected signal measurements of the field at additional locations within the organ using the model of the field.

Embodiments can include one or more of the following.

Modeling the field can include modeling the field based on physical characteristics of the organ. Modeling the field based on physical characteristics of fields can include using Laplace's equation. Modeling the field based on physical characteristics can include using Poisson's equation. Modeling the field based on physical characteristics can include modeling a homogeneous medium. Modeling the field based on physical characteristics can include modeling an inhomogeneous medium. Modeling of the field can include using a function that correlates field measurements with position coordinates. The function can be a differentiable function.

The current injecting electrodes can be mounted on one or more catheters that are placed inside the body. The current injecting electrodes can include one or more body-surface electrodes. The current injecting electrodes can include both electrodes mounted on one or more catheters that are placed inside the body and body-surface electrodes. The electrodes mounted on one or more catheters can include one or more electrodes secured to the organ. The electrodes mounted on the one or more catheters can include one or more electrodes that can be moved and positioned at multiple locations in an organ.

Obtaining the position of the one or more measuring electrodes can include using a tracking system to track the position of the one or more measuring electrodes. The tracking system can be a system using a magnetic field for tracking. The tracking system can be a system using injected currents for tracking.

Measuring the field can include measuring potentials.

The additional locations within the organ can include positions within the organ where the field was not measured. The positions within the organ where field was not measured can include positions that are more than 5 mm away from positions where the field was measured. The positions within the organ where field was not measured can include positions that are not lying between positions where the field was measured.

The method can also include determining a position of one or more additional electrodes in the organ based on measurements made by the additional electrodes and the determined expected signal measurements of the field. Determining a position of one or more additional electrodes in the field based on measurements made by the additional electrodes and the determined expected signal measurements of the field can include solving an optimization problem that minimizes collective difference between each of the measured signals and an estimate for each of the respective measured signals as a function of the position of the measurement.

Determining expected signal measurements can include determining expected signal measurements using a non-interpolation based calculation.

Modeling the field based on physical characteristics can include using the measured signals to determine an electric potential distribution produced by the current injecting electrodes on a surface enclosing the additional positions. The determination of the electric potential distribution can be based on an assumption of a homogenous conductivity within the surface. Modeling the field based on physical characteristics can be based on the electric potential distribution.

The current-injecting electrodes can operate at a frequency different from the frequency of normal electrical activity in the organ.

Obtaining the positions of the one or more measuring electrodes can include tracking coordinates for the multiple positions of the measured field.

The measuring of the field at the multiple locations can include moving a catheter having one or more measuring electrodes to multiple locations within the organ, and using the measuring electrodes to measure the field for each of the multiple locations of the catheter. The additional locations can correspond to regions inside the organ not interrogated by the movement of the catheter. The multiple sets of current-injecting electrodes can include at least three sets of current injecting electrodes and causing of the current flow can include causing current to flow between each set of current injecting electrodes. The field measured in response to the current flow can include an electric signal for each set of the current injecting electrodes for each of the multiple positions.

Modeling the field can include generating a field map.

The current injecting electrodes can be supported on one or more catheters, and at least one of the catheters further can include measuring electrodes for measuring at least some of the measured field.

The method can also include displaying the determined location of the measuring electrode relative to a surface of the organ.

The organ can be a patient's heart.

The field can be a scalar value field. The field can be a potential field. The field can be an impedance field.

In some aspects, a system includes a first catheter configured for insertion into an organ in a patient's body and comprising one or more measuring electrodes and multiple sets of current injecting electrodes. The system also includes an electronic control system coupled to the multiple sets of current injecting electrodes and to the one or more measuring electrodes. The control system is configured to cause current to flow among multiple sets of current injecting electrodes to generate a field in an organ and to measure the field and in response to the current flow, measure the field at multiple locations in the organ using the one or more measuring electrodes. The system also includes a tracking system configured to obtain the positions of one or more measuring electrodes used for measuring the field generated by the current injecting electrodes. The system also includes a processing system coupled to the electronic system. The processing system is configured to model the field using the measurements of the field from the one or more measuring electrodes and the positions of the one or more measuring electrodes and determine expected signal measurements of the field at additional locations within the organ using the model of the field.

Embodiments can include one or more of the following. The processing system can be further configured to model the field based on physical characteristics of the organ. The processing system can be further configured to model the field using Laplace's equation. The processing system can be further configured to model the field using Poisson's equation. The current injecting electrodes can be mounted on one or more catheters that are placed inside the body. The current injecting electrodes can include one or more body-surface electrodes. The current injecting electrodes can include both electrodes mounted on one or more catheters that are placed inside the body and body-surface electrodes. The electrodes mounted on one or more catheters can include one or more electrodes secured to the organ. The electrodes mounted on the one or more catheters can include one or more electrodes that can be moved and positioned at multiple locations in an organ. The tracking system can be a system using a magnetic field for tracking. The tracking system can be a system using injected currents for tracking. The multiple sets of current-injecting electrodes can include at least three sets of current injecting electrodes.

In some aspects an method includes (i) securing multiple sets of current injecting electrodes to an organ in a patient's body, (ii) causing current to flow among the multiple sets of current injecting electrodes to generate a field in the organ, (iii) in response to current flow caused by the multiple sets of current injecting electrodes, measuring the field at each of one or more additional electrodes, (iv) determining expected signal measurements of the field inside the organ using a pre-determined model of the field, and (v) determining a position of each of the one or more additional electrodes in the organ based on the measurements made by the additional electrodes and the determined expected signal measurements of the field.

Embodiments can include one or more of the following.

Determining the position of the one or more additional electrodes in the organ based on measurements made by the additional electrodes and the determined expected signal measurements of the field can include solving an optimization problem that minimizes a collective difference between each of the measured signals and an estimate for each of the respective measured signals as a function of the position of the measurement.

The estimate for each of the respective measured signals can include a differentiable function.

The one or more additional electrodes can include one or more electrodes used for delivering ablation energy for ablating tissue of the organ. The one or more additional electrodes can include one or more electrodes used for measuring the electrical activity of the organ.

The method can also include generating the pre-determined model of the field.

Generating the pre-determined model of the field can include causing current to flow among the multiple sets of current injecting electrodes to generate a field in an organ, obtaining the positions of one or more measuring electrodes, in response to the current flow, measuring the field at multiple locations in the organ using the one or more measuring electrodes, and modeling the field using the measurements of the field measured by the one or more measuring electrodes and the positions of the one or more measuring electrodes.

Modeling the field can include modeling the field based on physical characteristics. Modeling the field based on physical characteristics can include using Laplace's equation. Modeling the field based on physical characteristics can include using Poisson's equation. Modeling the field based on physical characteristics can include modeling a homogeneous medium. Modeling the field based on physical characteristics can include modeling an inhomogeneous medium. Modeling of the field can also include representing the model using a function that correlates field measurements with position coordinates.

The pre-determined model of the field can be a field map. The field map can be a function that correlates the expected signal measurements with position coordinates within the organ. The function can be a differentiable function.

Measuring the field can include measuring potentials.

The current-injecting electrodes can operate at a frequency different from the frequency of normal electrical activity in the organ.

The organ can be a patient's heart.

In some aspects, a system includes multiple sets of current injecting electrodes configured to be secured to an organ in a patient's body. The system also includes one or more additional electrodes configured to be positioned within the organ in the patient's body. The system also includes an electronic control system coupled to the multiple sets of current injecting electrodes and the one or more additional electrodes. The electronic control system can be configured to cause current to flow among the multiple sets of current injecting electrodes to generate a field in the organ. The electronic control system can also be configured to, in response to current flow caused by the multiple sets of current injecting electrodes, measure the field at each of one or more additional electrodes. The system also includes a processing system coupled to the electronic system. The processing system can be configured to determine expected signal measurements of the field inside the organ using a pre-determined model of the field and determine a position of each of the one or more additional electrodes in the organ based on the measurements made by the additional electrodes and the determined expected signal measurements of the field.

Embodiments can include one or more of the following.

The processing system can be configured to solve an optimization problem that minimizes a collective difference between each of the measured signals and an estimate for each of the respective measured signals as a function of the position of the measurement. The one or more additional electrodes can be one or more electrodes used for delivering ablation energy for ablating tissue of the organ. The one or more additional electrodes can be one or more electrodes used for measuring the electrical activity of the organ. The processing system can be further configured to generate the pre-determined model of the field.

In some aspects, a method includes (i) securing at least three sets of current injecting electrodes to an organ in a patient's body, (ii) causing current to flow among the multiple sets of current injecting electrodes to generate a field in the organ, (iii) using a multi-electrode array located on a multi-electrode array catheter in the organ for tracking a position of the multi-electrode array catheter relative to the current injecting electrodes, (iv) measuring the field generated by the current injecting electrodes in multiple locations in the organ using the multi-electrode array, (v) modeling the field using the measurements and the positions, (vi) determining expected signal measurements of the field at additional locations within the organ based on the model of the field, and (vii) determining a position of one or more additional electrodes in the organ relative to the current injecting electrodes based on measurements made by the additional electrodes and the determined expected signal measurements of the field.

Embodiments can include one or more of the following.

The method can also include removing multi-electrode array catheter from the organ prior to determining the position of one or more additional electrodes in the organ. The one or more additional electrodes can include one or more electrodes mounted on one of more additional catheters. The one or more additional electrodes comprise one or more electrodes of the multi-electrode array.

Modeling the field based on physical characteristics can include using Laplace's equation. Modeling the field can include modeling the field based on physical characteristics. Modeling the field based on physical characteristics can include using Poisson's equation. Modeling the field based on physical characteristics can include modeling a homogeneous medium. Modeling the field based on physical characteristics can include modeling an inhomogeneous medium. Modeling of the field can also include representing the model using a function that correlates field measurements with position coordinates.

The additional locations within the organ can be positions within the organ where the field was not measured. The positions within the organ where field was not measured can be positions that are more than 5 mm away from positions where the field was measured. The positions within the organ where field was not measured can be positions that are not lying between positions where the field was measured. Determining a position of one or more additional electrodes in the field based on measurements made by the additional electrodes and the determined expected signal measurements of the field can include solving an optimization problem that minimizes collective difference between each of the measured signals and an estimate for each of the respective measured signals as a function of the position of the measurement. Determining expected signal measurements can include determining expected signal measurements using a non-interpolation based calculation.

Measuring of the field at the multiple locations can include moving a catheter having one or more measuring electrodes to multiple locations within the organ, and using the measuring electrodes to measure the field for each of the multiple locations of the catheter.

The additional locations can correspond to regions inside the organ not interrogated by the movement of the catheter.

The multiple sets of current-injecting electrodes can include at least three sets of current injecting electrodes, and wherein the causing of the current flow comprises causing current to flow between each set of current injecting electrodes, and wherein the field measured in response to the current flow comprise an electric signal for each set of the current injecting electrodes for each of the multiple positions.

Modeling the field can include generating a field map.

The method can also include displaying the determined location of the measuring electrode relative to a surface of the organ.

In some aspects, a system can include at least three sets of current injecting electrodes configured to be secured to an organ in a patient's body. The system can also include a multi-electrode array catheter comprising a multi-electrode array configured to be inserted in the organ for tracking a position of the multi-electrode array catheter relative to the current injecting electrodes. The system can also include an electronic control system coupled to at least three sets of current injecting electrodes and to the multi-electrode array catheter. The electronic control system can be configured to cause current to flow among the multiple sets of current injecting electrodes to generate a field in the organ and measure the field generated by the current injecting electrodes in multiple locations in the organ using the multi-electrode array. The system can also include a processing system coupled to the electronic system. The processing system can be configured to model the field using the measurements and the positions, determine expected signal measurements of the field at additional locations within the organ based on the model of the field, and determine a position of one or more additional electrodes in the organ relative to the current injecting electrodes based on measurements made by the additional electrodes and the determined expected signal measurements of the field.

Embodiments can include one or more of the following.

The one or more additional electrodes can be one or more electrodes mounted on one of more additional catheters. The one or more additional electrodes can be one or more electrodes of the multi-electrode array. The multiple sets of current-injecting electrodes can include at least three sets of current injecting electrodes.

Embodiments of the system may also include devices, software, components, and/or systems to perform any features described above in connection with the first method and/or described below in connection with the second method.

Embodiments of the methods and systems generally disclosed herein can be applied to determining the position of any object within an organ in a patient's body such as the patient's heart, lungs, brain, or liver.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes; or any subset of such values.

As used herein, "heart cavity" means the heart and surrounding tissue.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

Figure 1:
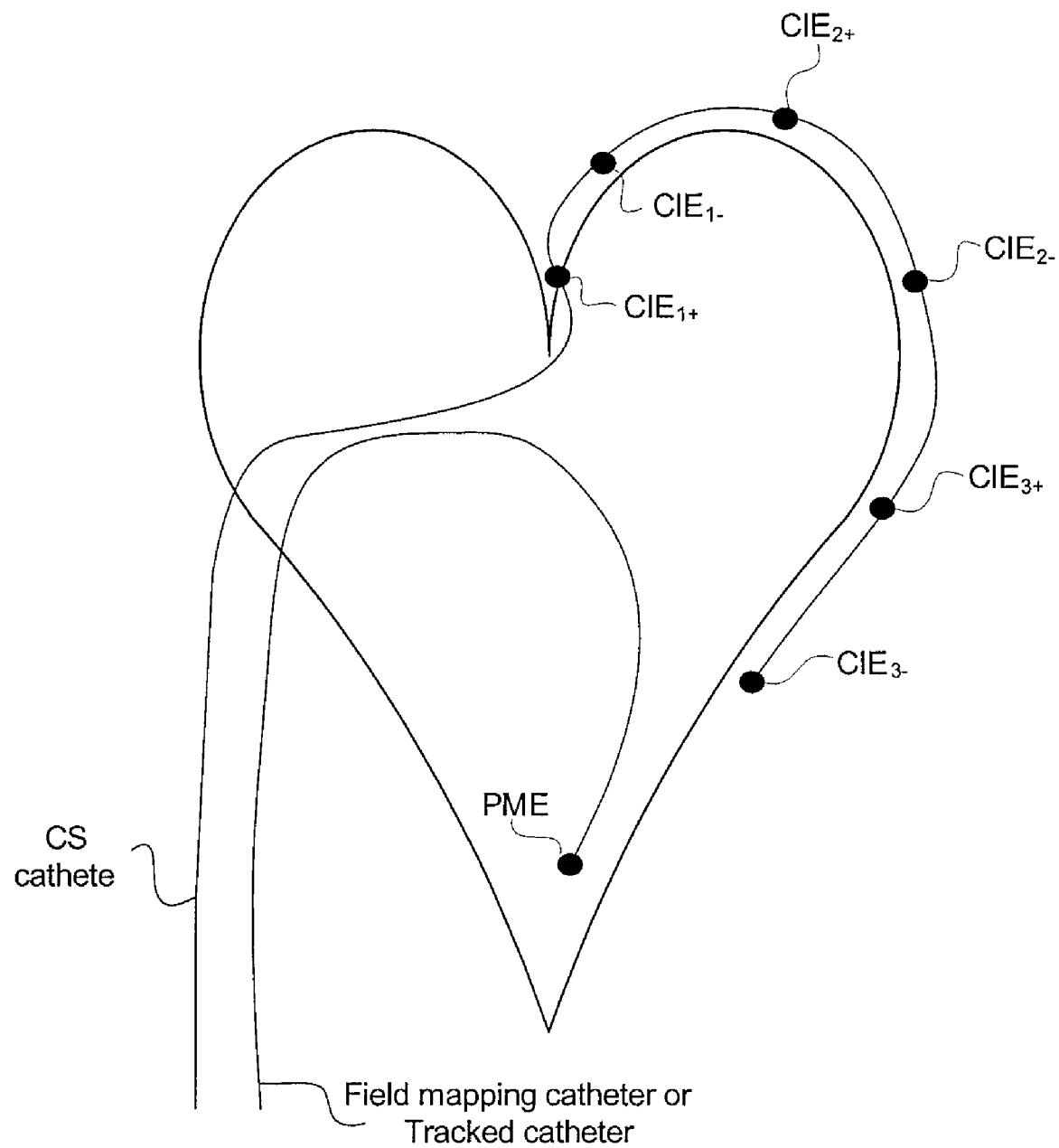
FIG. 1 is an exemplary schematic diagram of an arrangement for positioning current injection electrodes (CIE) and potential measuring electrodes (PME) with respect to a patient's heart cavity.

Embodiments disclosed herein include a method and system for determining the position of a catheter in a patient's heart cavity using a pre-determined model of the field that provides expected signal measurements of the field at various locations within the heart cavity.

More particularly, the methods and systems described herein provide a method for tracking electrodes mounted on catheters within and relative to the cardiac cavity, including any number of chambers within this cavity and the blood vessels surrounding it, but it can be used for tracking catheters in other body organs as well. Electrodes can be mounted on one or multiple catheters and by tracking these electrodes the location of such catheters can be determined and the catheters can be tracked. By knowing the physical characteristics of a catheter and the position of the electrodes on it, it is possible to track specific portion of the catheter (e.g., the tip) or to determine the shape and the orientation of the catheter (e.g., by using a spline fitting method on the location of multiple electrodes of the same catheter). Electrodes can also be mounted on other devices that require tracking inside the heart cavity.

In some aspects, the tracking is accomplished by generating a multitude of fields using current injecting electrodes (CIE) positioned and secured in a stable location (e.g., coronary sinus, atrial appendage, apex) and using measurements of the same fields on electrodes mounted on other catheters to locate the electrodes. The purpose of the CIEs is to inject current into the heart cavity. For example, each CIE pair can define a source and sink electrode, respectively, for injecting current into the heart cavity.

In general, in one aspect, a field mapping catheter that includes one or more potential measuring electrodes (PME) that can measure the fields (e.g., measure potentials in the heart cavity in response to the current provided by the CIEs) and at the same time can be tracked by an independent tracking system is used for generating a field map. The field map provides expected signal measurements of the field at various locations within the heart cavity. A field map is an example of a pre-determined model of the field. Other methods for generating a pre-determined model of the field exist and can be used. For example, a pre-determined model can be generated based on a volumetric image of the medium (CT or MRI) and an analysis of the medium based on that image to generate a physical model of the fields in the medium.

An independent tracking system can be any system for tracking catheters inside body organs, such as systems based on electric or magnetic signals generated externally and detected by one or more tracking elements, affixed to a catheter, or systems based on electric or magnetic signals generated internally from a catheter and detected by one or more sensors external to the body or internal to the body, affixed to other catheters The model of the field is generated using the field measurements and the positions measurements collected by the field mapping catheter. The model can be generated based on physical characteristics of the medium. Such a physical model can be determined, for example, by solving Laplace's equation in a homogeneous medium representing the cardiac chamber. The model of the field associates the field measurements to each location in space.

Once a field map is generated the independent tracking system can be turned off, any internal element of the system used to generate the field map can be taken out of the body, and the field mapping catheter can also be taken out of the body. However, the CIE used to generate the fields are left in their stable locations for subsequent use in tracking other electrodes. In some embodiments, removing the potential measuring electrodes used to generate the field map can be advantageous when it is desired to have fewer catheters inside the body organ for clinical reasons, or when certain tracking fields interfere with other instruments in the operating room. Using the field map it is possible to determine the location of any potential measuring electrodes (PME) that can measure the generated fields (e.g., the fields generated using the current injecting electrodes) inside the volume covered by the field map. The position of a tracked PME is determined by comparing the measured field value and the modeled field values. The position in the field map that holds a value matching the measurement of the tracked PME is assigned as the location of that PME.

In some embodiments, potentials measured in response to the injected current (e.g., tracking signals) can be used to continuously monitor the position of one or more catheters in the heart cavity, even as the catheters are moved within the heart cavity.

In the above discussion and in the details that follow, the focus is on determining the position of one or more catheters in a heart cavity for diagnosis and treatment of cardiac arrhythmias. However, this is only an exemplary application. The method and system generally disclosed herein could be used to track essentially any catheter mounted with at least one electrode, regardless of the catheter's intended function. Relevant examples include endocardial biopsies, therapies involving intra-myocardial injections of cells, drugs, or growth factors, and the percutaneous placement cardiac valves. In other examples, the method and systems generally disclosed herein can be applied to determining the position of any object within any distribution of materials characterized by a conductivity profile. For example, the methods and systems generally disclosed herein can be applied to determining the position of any object within an organ in a patient's body such as the patient's heart, lungs, brain, or liver.

Furthermore, while in some of the specific embodiments that follow the signals measured by the object electrodes correspond to the relative strength (e.g., amplitude) of the measured electrical signal (e.g., potential), further embodiments may also analyze the phase of the measured signal, either alone or in combination with the amplitude of the measured signal. The phase of the measured signal is indicative of spatial variations in the imaginary part of the complex conductivity (e.g., permittivity) in the distribution of materials.

In some aspects, the system tracks electrodes inside a body without having these electrodes injecting currents or emitting any field that needs to be detected. Rather, the fields can be generated by CIE positioned at fixed locations relative to the organ. This allows tracking of a large number of electrodes simultaneously, as the tracked electrodes are not polled one after the other as is the case with some other tracking methods.

In some additional aspects, the system does not require any external patches to be attached to the body, or any other external energy emitter. In some embodiments, the system only uses internal electrodes to inject currents. Furthermore, the method does not require any knowledge about the location in space of the current injecting electrodes.

In some embodiments, the CIE can be positioned such that the current injection is taking place from objects that are secured to the heart itself, reducing inaccuracies from motion artifacts that are experienced by systems that are referenced to an external coordinate system.

An inverse Laplace method is used to map the fields generated by the injected currents. An inverse Laplace method is more accurate than other methods used for volumetric field mapping (e.g., interpolation of measured values over the volume of interest). The field map generated by using the inverse Laplace method is more accurate in areas that were not probed specifically by the field mapping catheter and in areas not lying between positions that were probed.

In general, a field map generated by physical modeling of the medium, such as by using the inverse Laplace method, can be represented by a differentiable function. Finding a match between a measurement and the field map requires finding a minimum in the field using optimization. Optimization techniques of differentiable functions are believed to be faster and more accurate than other techniques.

FIG. 1 shows an exemplary schematic diagram of an arrangement for positioning current injection electrodes (CIE) and potential measuring electrodes (PME) with respect to a patient's heart cavity. Three CIE pairs (e.g., $CIE_{1+}$-$CIE_{1-}$; $CIE_{2+}$-$CIE_{2-}$; and $CIE_{3+}$-$CIE_{3-}$) are on a single catheter positioned and secured in a stable location in the coronary sinus, outside of any heart chamber. As described herein, while shown as positioned in the coronary sinus, other locations outside of the heart chamber, within the organ itself, and/or outside of the patient's body could be used to secure the CIE pairs.

A PME is mounted on another catheter that is placed within the cardiac chamber and can move relative to the cardiac chamber. The PME is able to measure the fields generated by the different CIE pairs. The catheter that supports the PME can be tracked by an independent tracking system and thus generate a model of the field, e.g., a field map, as described below. More particularly, the PME measures the fields generated by the CIE while at the same time being tracked by an independent tracking system. The measured fields and determined locations (e.g., from the independent tracking systems) are used to generate a model of the field, e.g., a field map, assigning field measurements to each location in space.

Once a model of the field is available it can be used for determining the position of any catheter capable of measuring the generated fields. Using the field map it is possible to determine the location of potential measuring electrodes (PME) that can measure the generated fields inside the volume covered by the field map. The position of a tracked PME is determined by comparing the measured field value and the modeled field values. The position in the field map that holds a value matching the measurement of the tracked PME is assigned as the location of that PME.

Tracking by Fields

Figure 2:
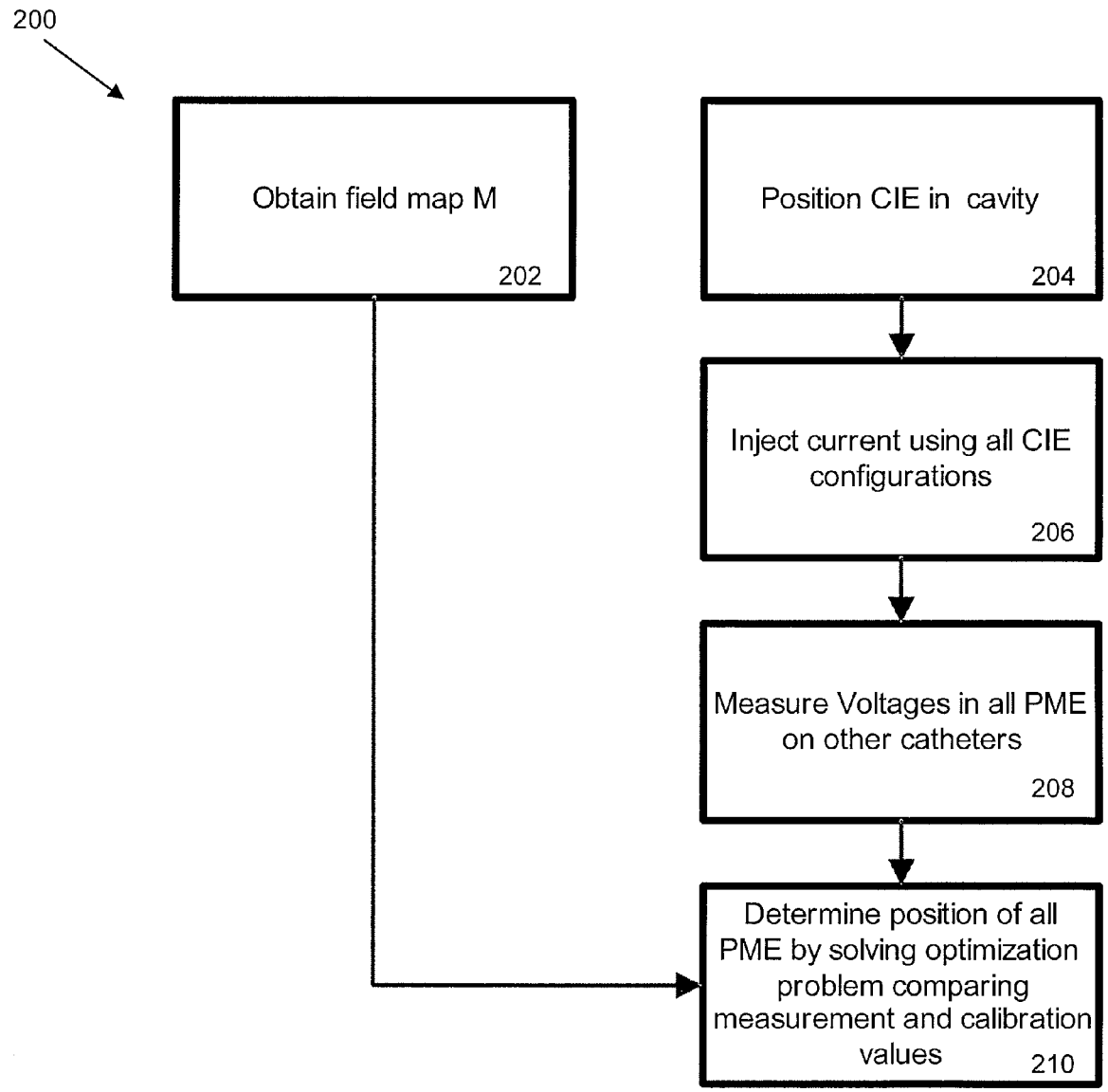
FIG. 2 is a flow diagram of an exemplary embodiment for determining the positions of PME.

Referring to FIG. 2, a process 200 for tracking electrodes (e.g., PME) using a pre-determined model of the field such as a field map is shown. In step 204, a number of current injecting electrodes (CIE), mounted on one or more catheters, are positioned in a stable position in the heart. The CIE are secured in a way that does not allow relative movement between the electrodes and the heart walls. For example, the CIE can be secured either by choosing a location such that the catheter will conform to the anatomy and will stay in a fixed position (e.g., coronary sinus or apex), or by using a fixation mechanism (e.g., anchoring mechanisms or a balloon mechanism). Information about the exact location of the catheter and the CIE is not necessary for tracking other catheters based on current injected by the CIE.

It should be noted that a minimum of three CIE configurations are necessary to span a three dimensional space and provide XYZ coordinates of other electrodes. An example of a CIE configuration is a pair of CIE configured as a dipole, having one CIE acting as a current source and the other CIE acting as a current sink. An electrode can be used in more than one CIE configuration. The electrodes cannot all be in the same plane or otherwise a 3D space cannot be spanned. For this reason a minimum of four CIE are needed.

In step 206, current is injected using the CIE configurations. In order to inject current an electrode must have impedance that is low enough. Low impedance can be achieved by a sufficient surface area or by using materials or coatings that lower the impedance of the electrode. Any low impedance electrode can be used for current injection and in a case where many or all electrodes on a certain catheter are capable of injecting current the designation of such electrodes as CIE on the catheter only indicates that these electrodes are actually being used for current injection.

Knowledge of the spatial configuration of CIE is not required for the tracking system to operate as long as the pairs used for injecting the currents are spanning the three dimensional space. Additionally, the properties of the medium and the inhomogeneity of the medium are not modeled and no prior knowledge is required about the medium.

It should be further appreciated that other configurations of CIE are possible as long as these configurations span the space. Examples of such a configuration could be quadruples involving 4 CIE, or even a non-symmetrical configuration involving 3 CIE. CIE electrodes can be on the same catheter or on different catheters. They can be in the same chamber, in different chambers or also in the cardiovascular system surrounding the heart. For simplicity the method using electrode pairs will be explained, but the same method can be applied using other configurations. In such cases there is still a need for at least three separate configurations in order to span the three-dimensional space and provide XYZ coordinates of other electrodes.

In step 208, potential measuring electrodes (PME) mounted on tracked catheters measure fields (e.g., potentials) emanating from cardiac activation, as well as the fields (e.g., potentials) generated by the CIE. A field can be any scalar field that associates a scalar value to every point in space. The PME can measure different kinds of fields, such as electrical potential field such as the potential in every point in space relative to a reference potential, an impedance field such as the impedance difference between every point in space to a reference point, etc. There is a need to distinguish between the cardiac activation signal and the signals from the CIE in order to separate the tracking signal being used for the location determination from the cardiac signal being used for generating the electrical activation maps. The CIE inject the current at a frequency higher than cardiac activation (cardiac activation <2 kHz, CIE>4 kHz, e.g., 5 kHz, 10 kHz, 25 kHz) such that the two types of signals can be distinguished using frequency analysis. It should be noted that other methods for distinguishing between the CIE signal and the cardiac activation signal can be used, such as injecting a spread-spectrum signal having a low energy level in the frequency range of the cardiac activation signal, and detecting this spread-spectrum signal in the signal collected by the all PME.

In order to span the space three separate configurations of CIE need to inject current (e.g., 3 pairs of CIE not residing in the same plane). There is a need to determine the source of the injected signal and to trace it to a specific CIE configuration. The three pairs of CIE inject the current sequentially, one pair at a time, so that it is possible to trace the source of the measured PME signals to a specific pair. This is called time division multiplexing. In the case of time division multiplexing, CIE are activated in sequence such that at one point in time one pair is activated (e.g., $CEI_{1+}$ and $CEI_{1-}$) and at the next point in time another pair is activated (e.g., $CIE_{2+}$ and $CIE_{2-}$). The switching between pairs may occur every cycle (e.g., ⅕ kHz=200 μs) or every few cycles (e.g., 20 cycles, 20×200 μs=4 mS). It should be noted that frequency or code division (spread spectrum) multiplexing, rather than time division may be used to separate the signals. In the case of frequency multiplexing all CIE pairs may inject the current at the same time, but each pair uses a different signal frequency. The signal collected at the PME is filtered according to the frequency, and the signal measured in each frequency is then associated with the appropriate originating pair.

In step 202, the system obtains a field map generated prior to the tracking of the PMEs. In general, the field map provides an expected field for a given location within the organ. In step 210, the tracking of the PME on the catheters is performed by solving an optimization problem that compares the measurement collected by the PME as a result of activation of the CIE pairs, to expected measurements in a given location provided in the field map. The location that minimizes the difference between the expected field and the measured field is assigned as electrode location. Exemplary methods for obtaining the field map are described in further detail below.

While in some of the specific embodiments that follow the signals measured by the object electrodes correspond to the relative strength (i.e., amplitude) of the measured electrical signal (e.g., potential), further embodiments may also analyze the phase of the measured signal, either alone or in combination with the amplitude of the measured signal. The phase of the measured signal is indicative of spatial variations in the imaginary part of the complex conductivity (e.g., permittivity) in the distribution of materials.

The field mapping process explained below provides a field map, M, assigning field measurements to each location in space. In case of three CIE pairs each location in space, $\rho=(x,y,z)$ being the location in 3D Cartesian coordinates, is assigned three measurements, $(V_1, V_2, V_3)$, corresponding to the three different fields generated by the three CIE pairs. The field map can be represented as a function $M(x,y,z) = (V_{E1}, V_{E2}, V_{E3})$, when $V_E$ stands for the expected voltage based on the field map.

Correspondingly, three measured results $(V_{M1}, V_{M2}, V_{M3})$ are also obtained from the tracked PME. The specific location will be computed such that ρ minimize the expression:

$$\min_{\rho} \left| \sum_{i=1}^{3} (V_{Mi} - V_{Ei})^2 \right| \qquad (1)$$

Equation (1) is a non-linear optimization problem. This problem is solved using an iterative scheme such as Newton-Raphson or Levenberg-Marquardt or a direct search method such as the Nelder-Mead Simplex Method.

In the case of more than three pairs of CIE the solution for ρ becomes overdetermined since we obtain more equations than unknowns, which helps improve tracking accuracy depending on the specific embodiment.

This method determines the location of PME without any prior knowledge of the CIE spatial configuration or any prior knowledge of the characteristics of the medium.

In some embodiments, more than one PME may be tracked simultaneously using process 200. To do so, signals are acquired from and an optimization problem is solved for each of the electrodes being tracked. If such electrodes are mounted on different catheters, it is possible to simultaneously track multiple catheters.

Systems that require the tracked electrode to inject current usually track a single electrode at any given time, and for the tracking of multiple electrodes such systems usually activate one electrode at a time and sequentially cycle through all tracked electrodes. Since there is a minimum duration that each electrode needs to be active in such a system, and there is also a desired refreshing rate for the tracked location, there is a limit to the number of electrodes that can be tracked simultaneously in such systems. Due to the passive nature of the tracked PME in the disclosed invention there is no limit to the number of PME that can be tracked simultaneously.

As noted above, the measurements collected at the PMEs as a result of current injected by the CIE are generally affected by the complex conductivity, or admittivity, distribution of the medium. While the specific embodiment discussed above focus on the real part of the conductivity which affects the amplitude measured by the PMEs, additional information can also be obtained by accounting for the real part (conductivity) and imaginary part (permittivity) of the medium's complex conductivity, which affects the amplitude and phase of the signal measured by the PME. In this manner, the use of both amplitude and phase, or phase alone may also be used for tracking purposes. Use of the imaginary part of the complex conductivity is of particular importance in material distributions where the permittivity contrast exceeds that of the conductivity contrast.

To modify the mathematical formalism for the specific embodiments described above to account for imaginary part of the complex conductivity each location in space, $\rho=(x,y,z)$ being the location in 3D Cartesian coordinates, is assigned three complex measurements, $(V_1^*, V_2^*, V_2^*)$. The fields map can be represented as a complex function $M(x,y,z)=(V^*_{E1}, V^*_{E2}, V^*_{E3})$.

Correspondingly, three complex measured results $(V^*_{M1}, V^*_{M2}, V^*_{M3})$ are also obtained from the tracked PME. The specific location will be computed such that $\rho$ minimize the expression:

$$\min_{\rho} \left| \sum_{i=1}^{3} (V_{Mi}^* - V_{Ei}^*)^2 \right| \quad (2)$$

Equation (2) can be solved using the similar methods used for solving equation (1).

Generating the Field Map

As described above, the field map is a function, M, which correlates scalar measurements of the fields generated by the different CIE sets with position coordinates of an independent tracking system. An independent tracking system is one of any tracking systems that exist for tracking catheters inside body organs. Such a system can be based, for example, on tracking electric or magnetic signals generated externally and detected by one or more tracking elements, such as sensors, affixed to a catheter. Alternatively, tracking elements such as emitters or beacons affixed to the catheter may emit electric or magnetic signatures that are detected by an independent tracking system, and used to determine the location of the emitters, and thus the location and orientation of a catheter. For example, a collection of miniaturized coils oriented to detect orthogonal magnetic fields and forming a sensor can be placed inside the catheter to detect the generated magnetic fields. The independent tracking systems are often disposed outside the patient's body at a distance that enables the system to either generate radiation of suitable strength (i.e., generate signals whose amplitude will not harm the patient or otherwise interfere with the operation of other apparatus disposed in the near vicinity of the sensing and tracking system), or detect magnetic or electric radiation emitted by the emitters affixed to a catheter.

Pending patent application Ser. No. 12/061,297 entitled "Intracardiac Tracking System" and filed Apr. 2, 2008, whose disclosure is incorporated herein in its entirety by reference, describes an alternative independent tracking system utilizing a multi-electrode array (MEA) for generating and sensing fields in the cavity for tracking PME and catheters. The system utilizes reference electrodes secured in stable positions to reference the tracking coordinate system to the organ, compensating for movement of the cavity in space that can result from different reasons such as patient movements or patient respiration.

In case the independent tracking system generates fields in the medium by injecting currents there is a need to determine the source of the measured field signal and to trace it to a specific origin. It is possible to use separate frequencies for the two systems, for example use 5 KHz for the independent tracking system and 12 KHz for the currents injected by the CIE of the disclosed invention. The signal collected at the PME is filtered according to the frequency, and the signal measured in each frequency is then associated with the appropriate originating system. It is also possible to inject the current sequentially, one set at a time, cycling through the current injecting sets of the independent tracking system and the CIE sets of the disclosed invention, so that it is possible to trace the source of the measured PME signals to a specific source. This way the time division multiplexing is used for both systems in a synchronous way. It should be noted that spread spectrum can also be used for the CIE of the disclosed invention to prevent interference with the independent tracking system while keeping the ability to detect the injected field and to measure it.

The field mapping process uses a catheter that can be tracked by the independent tracking system and that has at least one PME that can measure the fields generated by the CIE. The MEA catheter described in pending patent application Ser. No. 12/061,297 entitled "Intracardiac Tracking System" and filed Apr. 2, 2008 is an example of a catheter that can be used for the field mapping process. The catheter used can be referred to as the field mapping catheter.

Figure 3:
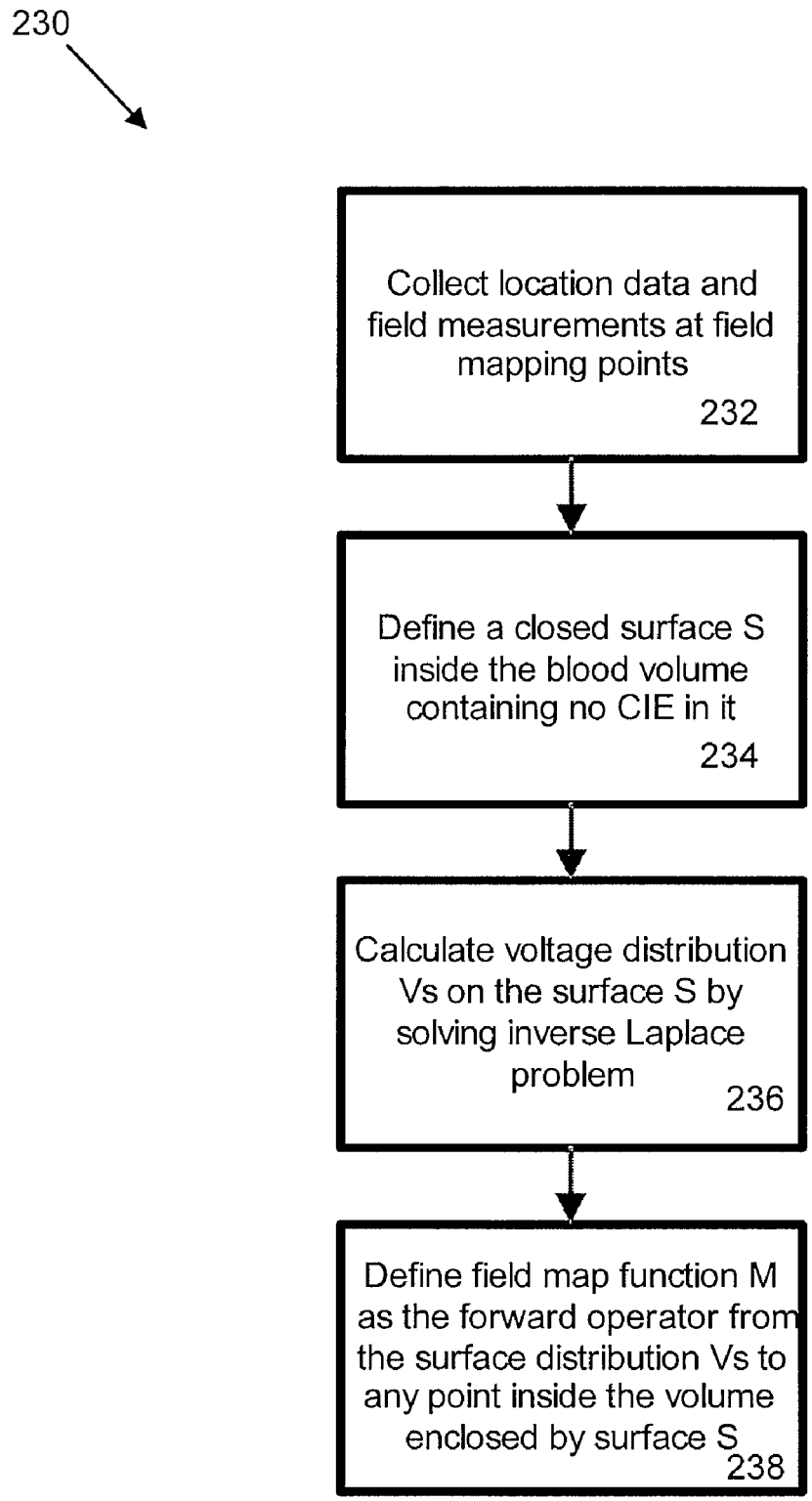
FIG. 3 is a flow diagram of an exemplary embodiment for generating a field map.

Referring to FIG. 3, a process for generating a field map is shown. In step 232, the system collects location data and field measurements at field mapping points. More particularly, the field mapping catheter is moved around inside the organ of interest while being tracked by the independent tracking system and while measuring the generated fields of the CIE that are secured in fixed locations relative to the organ. While the example shown in FIGS. 1, 4, and 5 includes three CIE pairs on a single catheter positioned outside of any heart chamber various locations (e.g., other locations outside of the heart chamber, within the organ itself, and/or outside of the patient's body) could be used to secure the CIE pairs.

The processing unit in the tracking system records the location in space of the field mapping catheter and stores for each location the field measurements measured by the PME of the field mapping catheter. For example, in the case of three CIE pairs each location in space, $\rho=(x,y,z)$ being the location in space in the coordinate system of the independent tracking system, is assigned three measurements, $(V_1, V_2, V_3)$. The processing unit stores a table holding the different locations and the different measurements $T(x_i, y_i, z_i) = (V_{i1}, V_{i2}, V_{i3})$, i being the index number of the stored location. The locations in which the fields were sampled and the results were stored in the table T are referred to as field mapping points (FMP).

Cardiac contraction changes the medium in which the fields are being generated thus changing generated fields. For that reason the field measurements are gated according to the cardiac cycle. This can be done by using electrical measurements of the cardiac cycle (e.g., by the use of surface ECG) and triggering on a constant marker in the cardiac phase (e.g., using an R-wave detection algorithm, a threshold criterion, or a maximum criterion). Another option is to use a measurement that is affected directly by the mechanical movement of the heart, such as the measurement of the impedance between CIE, which changes as the distance between them changes as the heart contracts, and triggering on a constant marker in the cycle. Once a trigger is determined the cardiac cycle is divided into m slices (e.g., m=10), and the mentioned recording is repeated for each slice separately. This method results in m separate tables, $T_m(x_{i,m}, y_{i,m}, z_{i,m}) = (V_{i1,m}, V_{i2,m}, V_{i3,m})$, each one should be used for the appropriate phase of the heart cycle.

The table holding the locations and the measurements, T, is used for generating the field map M. Field map M is a function providing fields measurements for each location in space, for example $M(x,y,z) = (V_{E1}, V_{E2}, V_{E3})$ in the case of three CIE pairs. The function needs to provide field values with spatial resolution corresponding to the required accuracy of the tracking system.

Figure 4:
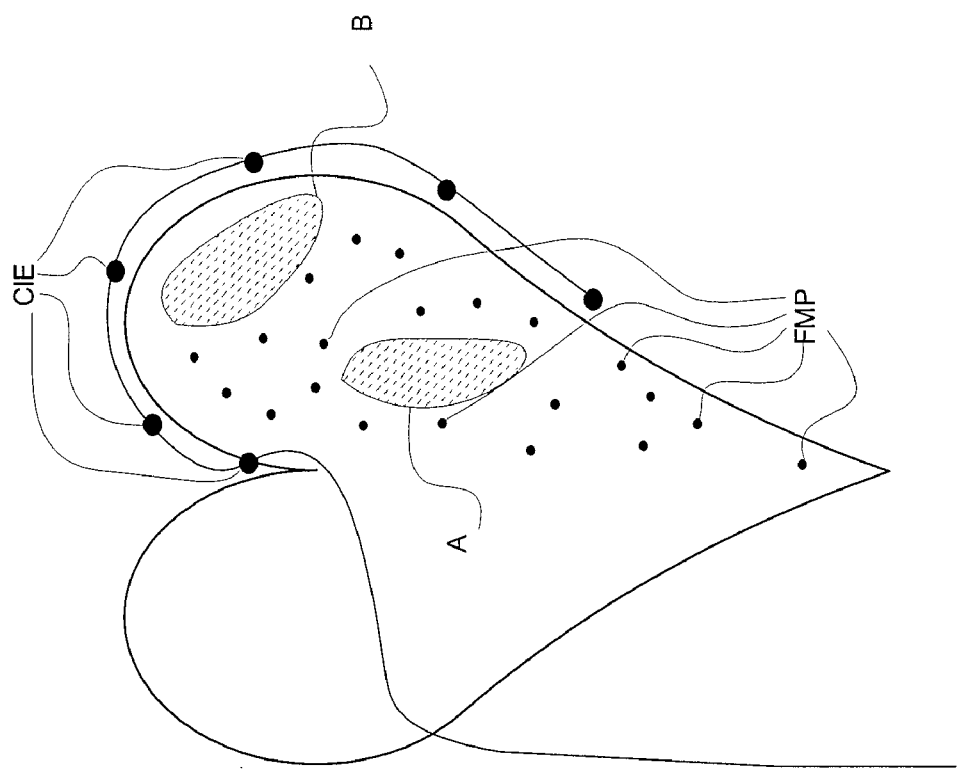

One way to generate function, M, from the data table, T, is to generate a 3D grid, G, with a resolution that fits the required accuracy of the tracking system and use interpolation techniques on the values in table T. An interpolation algorithm, such as cubic interpolation, is used to interpolate the values stored in T onto G. The function M is defined as the interpolated values on the grid G. When using the interpolation method for generating the field map function the resolution of the tracking system is limited by the resolution of the interpolation grid and by the accuracy of the interpolation itself. Furthermore, the function M generated in this method is not differentiable by definition, and therefore not all schemes mentioned for solving the minimization problem above are applicable. Solving the minimization problem for determining the location is slower in this case. Another disadvantage of this method is low accuracy in regions that have a large distance between FMP. For example, FIG. 4 shows an exemplary schematic diagram of an arrangement for positioning current injection electrodes (CIE) and potential measuring electrodes (PME) with respect to a patient's heart cavity. While the example shown in FIG. 4, includes three CIE pairs on a single catheter positioned outside of any heart chamber other locations outside of the heart chamber, within the organ itself, and/or outside of the patient's body could be used to secure the CIE pairs. The schematic diagram of FIG. 4 also shows multiple field mapping points (FMP) with respect to a patient's heart cavity. In the example shown in FIG. 4, the area marked "A" exhibits a large distance between FMP and therefore the accuracy determined using an extrapolation/interpolation technique would be lower in area A. Additionally, areas that are not lying between FMP (such as the area marked "B" in FIG. 4) require extrapolation, which has lower accuracy as the distance from the FMP increases.

As described above, using extrapolation/interpolation to generate the function M can result in a lower accuracy for points that are not located near the FMP. Rather than using extrapolation/interpolation, the field map function, M, can be generated by modeling the field. Modeling the field can provide a powerful tool for tracking the location of electrodes within an organ because the model of the field can provide a higher accuracy in the expected signal measurements than using an extrapolation/interpolation technique to generate the function. Modeling the field uses the measurements of the field from measuring electrodes and the positions of the measuring electrodes to determine expected signal measurements of the field at additional locations within the organ. Modeling the field can use a mathematical calculation, such as Laplace's equation or Poisson's equation, that takes into account the physical characteristics of organ, for example by modeling a portion of the organ as a homogeneous medium. Unlike an extrapolation/interpolation based technique, modeling the field generates a function that is differentiable. Since finding a match between a measurement and the field map includes finding a minimum in the field using an optimization, providing a differentiable function for the field map is believed to enable the user of faster and/or more accurate optimization techniques.

Figure 5:
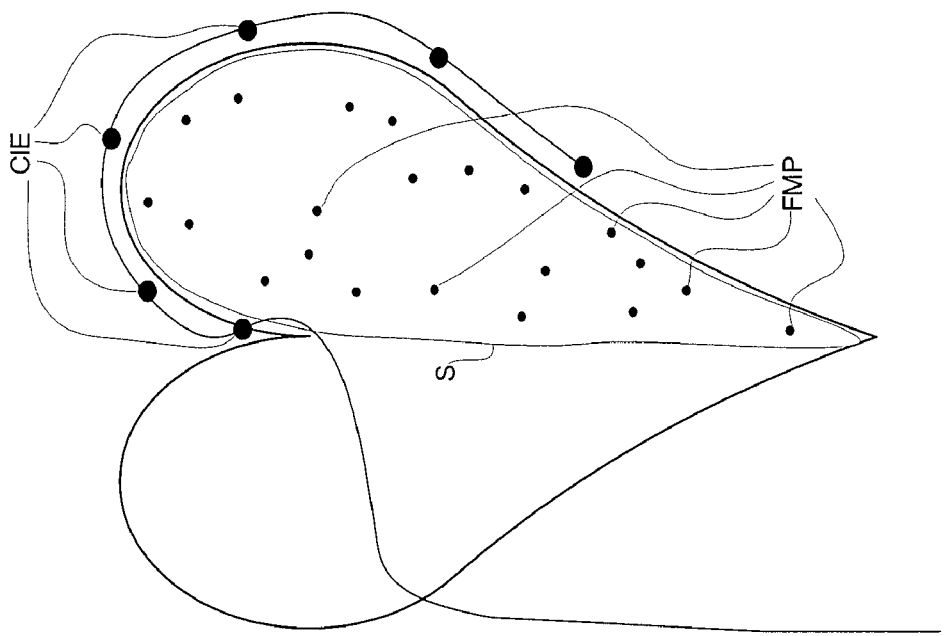
FIGS. 4 and 5 are exemplary schematic diagrams of an arrangement for positioning current injection electrodes (CIE) and potential measuring electrodes (PME) with respect to a patient's heart cavity.

An example of a method of generating the field map function, M, by modeling the field is the use of inverse theory. FIG. 5 shows an exemplary schematic diagram of multiple field mapping points (FMP) and a defined closed surface, S, encompassing the FMP but not enclosing the CIE. Referring back to FIG. 3, as described above in relation to step 232, the potential field generated as a result of the injected current from the CIE can be the field measured by the PME in the blood volume of the cavity. In step 234, a closed surface, S, is defined inside the blood volume having no CIE in it. Because blood is a homogenous medium and the volume inside that closed surface has no sources (e.g., no CIE), the CIE can be modeled as a voltage distribution outside that closed volume. This voltage distribution gives rise to an unknown Dirichlet boundary condition, or voltage distribution, on the closed surface. In step 236, the voltage distribution Vs on the surface S can be calculated, for example by solving an inverse Laplace problem as described below.

In another example, if the CIE are positioned outside of the cardiac chamber, it is possible to use the surface of the chamber's anatomy as the closed surface having the Dirichlet boundary condition. The anatomy of the chamber can be generated using the independent tracking system at the time of the field map generation. In some embodiments, the anatomy can be generated using a point cloud method, such as the method disclosed, for example, in U.S. Pat. No. 6,226,542 the contents of which is incorporated by reference herein. Another option to obtain the anatomy is registering a segmented imaging modality (e.g., a CT scan of the organ) to the coordinate system of the independent tracking system. An example of the use of an imaging modality is disclosed, for example, in patent application Ser. No. 11/451,898, entitled "NON-CONTACT CARDIAC MAPPING, INCLUDING MOVING CATHETER AND MULTI-BEAT INTEGRATION" and filed Jun. 13, 2006, the contents of which is incorporated by reference herein. When generating the anatomy it is desired to use the phase of the cardiac cycle that will be later used for tracking. This can be done similar to the ways mentioned above for accounting for the contraction cycle when collecting the field mapping points using PME. It is also possible to use several anatomical representations, one corresponding to each phase of the cardiac cycle, m, and use the multiple representations for generating different field maps, one for each phase of the cardiac cycle.

In general, the surface, S, can be modeled as having a voltage distribution Vs representing the field sources. The field inside the volume contained by surface S will follow Laplace's equation. In other words, the measurements collected by PME can be treated as a propagation of the voltage distribution Vs from the surface S to the PME which follows Laplace's equation. It follows that the voltage distribution Vs can be computed using an inverse Laplace algorithm based on measurements collected by PME in the field mapping process and stored in table T. In this manner the field in the entire volume can be calculated from the boundary condition Vs generated by the inverse Laplace algorithm on the data stored in table T. Referring again to FIG. 3, in step 238, a field map function M is generated as the forward operator from the surface distribution Vs onto any point inside the volume enclosed by the surface. An exemplary a method to compute all the fields at any location inside the closed surface (e.g., a method to compute field map function M) using inverse theory is described below. It should be noted that to perform the computation a surface S is constructed that is contained in the blood volume and does not contain any CIE.

For each field generated by a CIE set the inverse procedure is done separately, and the process is repeated for all CIE sets (for example three times if the minimum of 3 CIE sets are used).

The physical laws governing the reconstruction of the field representation on at the surface S are briefly summarized below:

The potential V in a homogeneous volume $\Omega$ is governed by Laplace's equation $$\nabla^2 V = 0 \qquad (3)$$

subject to boundary conditions $$V=V_s \text{ on surface } S \quad (4)$$

where S represents the surface for solving the boundary condition.

Numerical methods such as boundary element method (BEM), finite element method (FEM), finite volume method, etc. may be used to solve Laplace's equation. Each numerical method represents the geometry and signal using basis functions, but each method uses its own representation. In all numerical methods the potentials on the surface and on the field mapping points (FMP) are represented by finite-dimensional vectors. Since Laplace's equations are linear, these vectors are related by a matrix A, known as the forward matrix:

$$V_{FMP1} = A \cdot V_{S1} \quad (5)$$

$V_{FMP1}$ is the vector containing the measurements of the field generated by the first set of CIE in the field mapping points (FMP). The vector has the dimension n×1 where n is the number of FMP that were recorded during the field mapping process. $V_{S1}$ is a vector containing the voltage distribution on surface S while the first CIE set is active.

The matrix A has dimensions of n×m, where n is the number of FMP locations and m is the number of degrees of freedom in the surface potential, usually the number of surface elements used to represent the surface S.

It is important to note that the 3D coordinates of FMP are used for the construction of A.

Equation 5 provides a forward relationship between surface voltage $V_{S1}$ and the FMP voltages $V_{FMP1}$. In the field mapping problem surface voltage $V_S$ is unknown while the measured FMP voltages $V_{FMP1}$ are known. An inverse relationship is employed to solve for $V_S$. This inverse relationship may be posed as a least squares optimization problem:

$$\min_{\hat{V}_S} \left( \| A \cdot \hat{V}_{S1} - V_{FMP1} \|^2 + \alpha \cdot \| L \cdot \hat{V}_{S1} \|^2 \right) \quad (6)$$

Where $V_{FMP1}$ are measured potentials, A is the forward operator as defined in equation 5, $\alpha$ is a regularization parameter, L is a regularization operator, and $\hat{V}_{S1}$ is the vector representing the unknown surface voltage that is being calculated. Examples of the use of inverse theory and regularization are described, for example, in patent application Ser. No. 11/451,898, entitled "NON-CONTACT CARDIAC MAPPING, INCLUDING MOVING CATHETER AND MULTI-BEAT INTEGRATION" and filed Jun. 13, 2006, the contents of which is incorporated by reference herein.

Tikhonov regularization may be used in this case. In the case of Tikhonov 0 regularization operator L is the identity matrix, while in the case of Tikhonov 1 L is the gradient operator on surface S. In some examples, Tikhonov 1 outperforms Tikhonov 0 and a regularization parameter $\alpha=0.1$ is found to be effective.

It should be noted that in order to determine $\hat{V}_{S1}$ there is no need to move the field mapping catheter through the entire volume contained inside the surface S. Further, the density of FMP does not have to be the same as the required resolution of the tracking system. It is preferred to have FMP points close (e.g., about 5 mm) to the surface area that is closest to the CIE in order to model the CIE effect on the surface S with high spatial resolution. The inverse theory projects the available measurements on the surface and allows computing the field anywhere inside the enclosed volume.

With $\hat{V}_{S1}$ known, it is possible to compute the expected voltage measurement anywhere inside surface S in a manner identical to equation 5, except that it is done for a particular location of interest.

The process is repeated for all generated fields. This results in several separate boundary conditions $\hat{V}_{Sj}$. In the case of three CIE pairs, for example, j=3. In this example the field map function M is defined as $M(x,y,z)=(A_{x,y,z} \cdot \hat{V}_{S1}, A_{x,y,z} \cdot \hat{V}_{S2}, A_{x,y,z} \cdot \hat{V}_{S3})$ where $A_{x,y,z}$ is defined as the forward matrix for calculating the field in location x,y,z from the boundary distribution on the surface S.

This method generates a field map function M which is accurate for the entire enclosed volume using inverse Laplace theory.

Similar methods can be used for generating field maps for different kinds of scalar fields. An impedance field can be generated using the same inverse approach to achieve an accurate and differentiable impedance field map without interpolation. In the case where there are electrodes injecting currents inside the volume, such as the case in which the field mapping catheter is involved in the current injection, a similar inverse method can be used. In such a case instead of using Laplace's equation a more general representation of the electrical distribution, called Poisson's equation, can be used. Similar tools can be used for solving the inverse Poisson problem and generating a field map.

Figure 6:
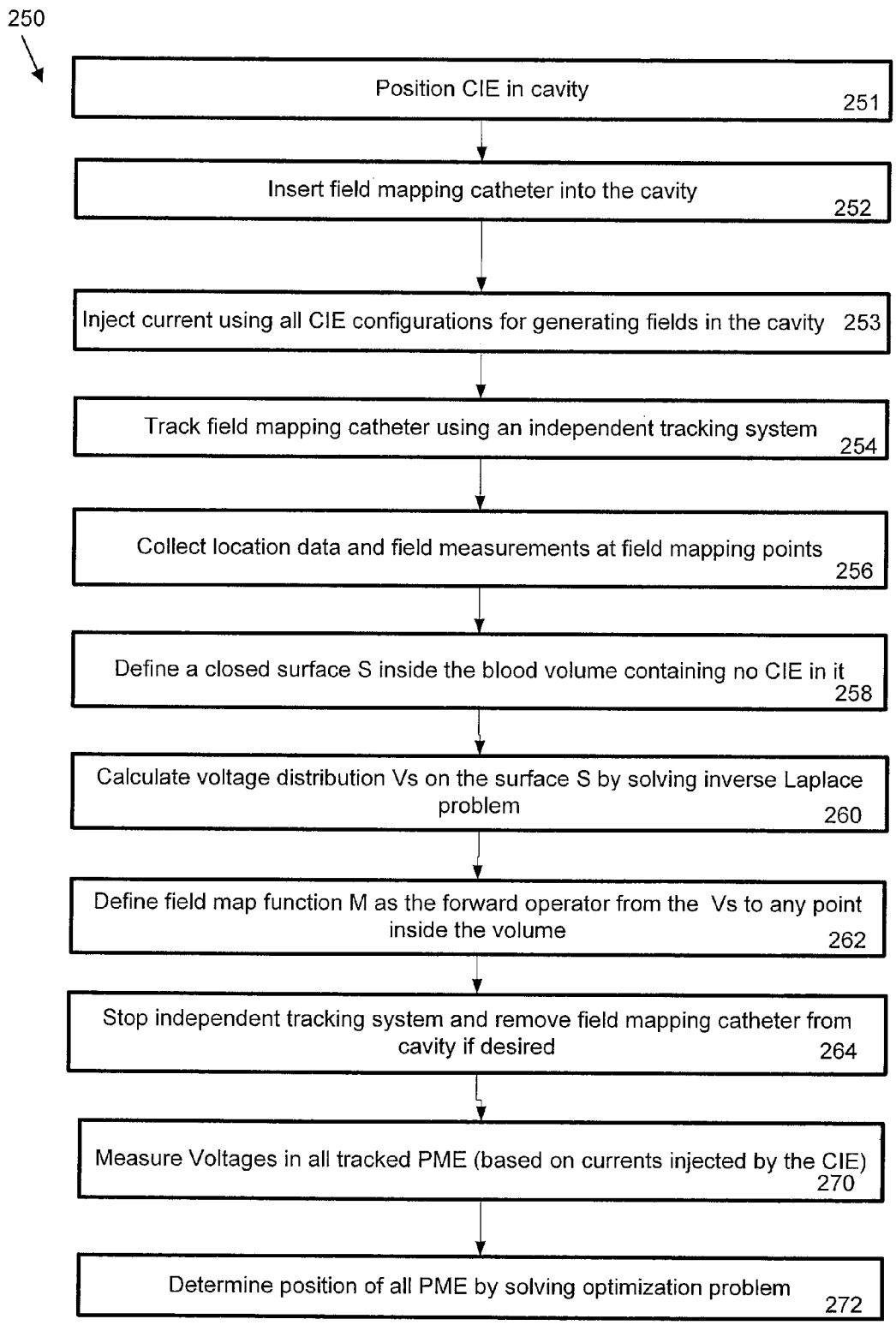
FIG. 6 is a flow diagram of an exemplary embodiment for generating a field map and using the field map to determine the positions of PME.

Referring to FIG. 6, in some examples generating the field map and tracking by fields using the field maps, can be combined and executed in a single sequence on a patient using multiple catheters. Process 250 describes a method for determining the position of PME within an organ using a field map in which the catheter used to generate the field map can be removed prior to tracking the location of the PME. For example, PME on one catheter can be used to generate the field map which is used to track PME on another catheter such as an ablation catheter. In step 251, current injecting electrodes are positioned in the cavity. The CIE are used both for providing the signals used in generating the field map and for providing the signals used in tracking the locations of PME using the field map. In step 252, a catheter for field mapping is inserted into the cavity. In step 253, current is injected using the CIE. In step 254, the field mapping catheter is tracked by an independent tracking system. In step 256, location data and field measurements are collected at multiple field mapping points within the cavity. In step 258 a closed surface, S, inside the volume and not including the CIE is generated. In step 260, the voltage distribution on the surface is calculated. Using the calculated voltage distribution, in step 262, a field map is defined as the forward operator from the surface to any point inside the volume enclosed by the surface. Once a sufficient field map is generated, in step 264, the independent tracking system can be turned off, any internal element of that system can be taken out of the body, and the field mapping catheter can also be taken out of the body. This is advantageous when it is desired to have fewer catheters inside the body organ for clinical reasons, or when certain tracking fields interfere with other fields. In step 270, the voltages on the tracked PME are measured. The fields measured by the PME are generated using the CIE (e.g., as described in step 268). In step 272, the position of the PME is determined by solving an optimization problem using the previously generated field map.

Figure 7:
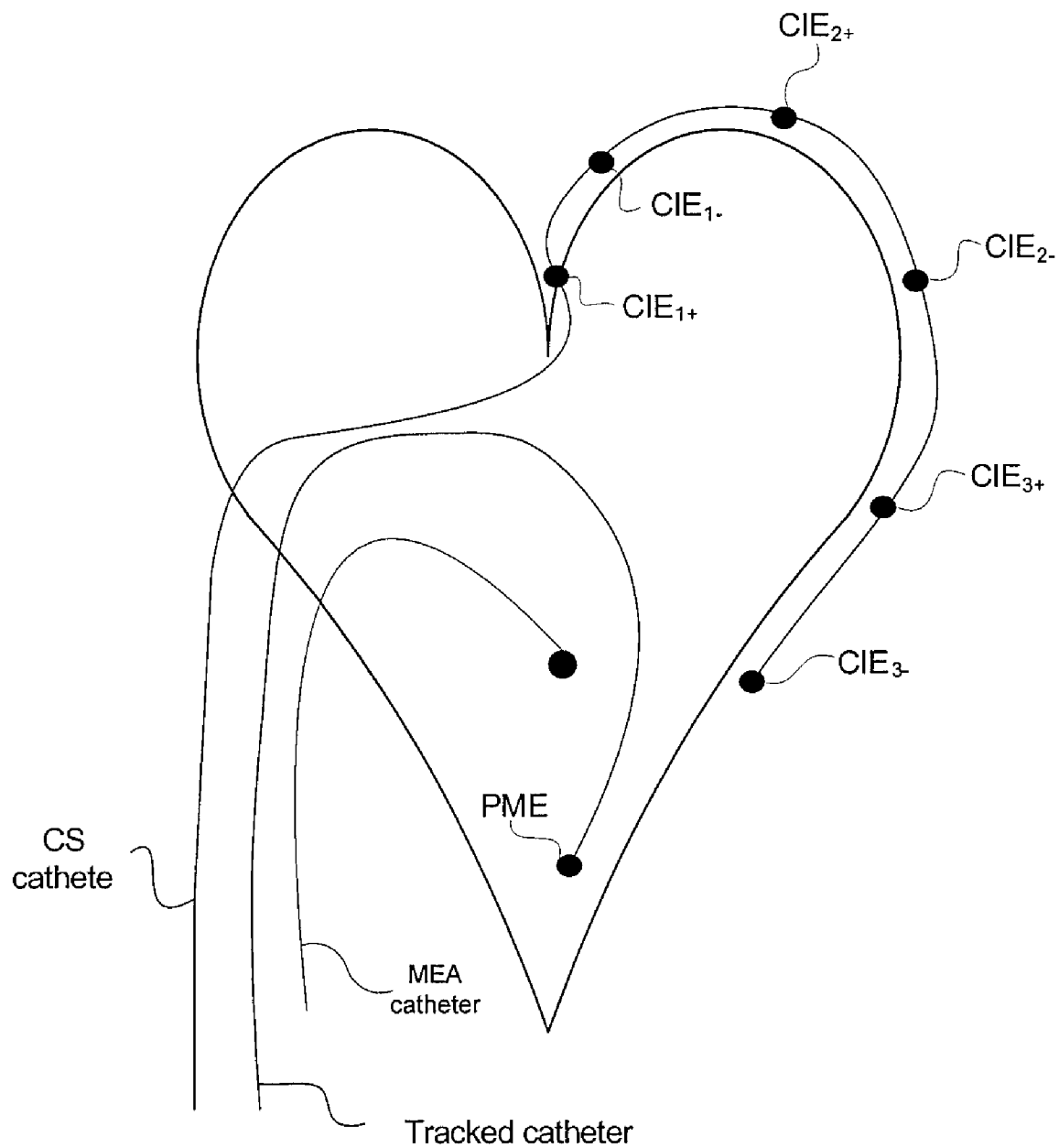
FIG. 7 is an exemplary schematic diagram of an arrangement for positioning current injection electrodes (CIE), potential measuring electrodes (PME), and a multi-electrode array (MEA) catheter with respect to a patient's heart cavity.

As noted above, in some embodiments, a multi-electrode array can be used to determine the location of the electrodes within the organ while collecting measurements of the fields to generate the field mapping points. FIG. 7 shows an exemplary schematic diagram of an arrangement for positioning current injection electrodes (CIE), a multi-electrode array (MEA) catheter, and potential measuring electrodes (PME) with respect to a patient's heart cavity.

Three CIE pairs (e.g., CIE1+-CIE1-; CIE2+-CIE2-; and CIE3+-CIE3-) are on a single catheter positioned and secured in a stable location in the coronary sinus, outside of any heart chamber. The placement of the CIE pairs in the coronary sinus provides a fixed location for the CIE pairs. As described herein, while shown as positioned in the coronary sinus, other locations outside of the heart chamber, within the organ itself, and/or outside of the patient's body could be used to secure the CIE pairs.

Using an MEA catheter provides an alternative to using an independent tracking system for tracking PME and catheters while generating the field mapping points. An exemplary MEA catheter is described in Pending patent application Ser. No. 12/061,297, entitled "Intracardiac Tracking System" and filed Apr. 2, 2008 whose disclosure is incorporated herein in its entirety by reference. The exemplary MEA catheter includes CIE for the purpose of independently tracking its position and the positions of other PME and catheters. The same MEA catheter can also be used for the field mapping process. In general, in the description below, three catheters are used: (1) A MEA catheter is used for generating the field map (2) another catheter (referred to as the tracked catheter) is tracked based on the generated field map (3) a catheter that includes CIE is secured to secured to a stable position. For simplicity, the CIE mounted on the MEA catheter will be referred to as "MCIE" while the CIE of the current invention, that are secured to a stable position and that are used for field mapping and for tracking of PME based on that map, will be referred to as the "SCIE." For simplicity, the PME mounted on the MEA catheter will be referred to as "MPME" and the PME mounted on the tracked catheter will be referred to as "TPME." While the example described above uses three catheters (e.g., the MEA catheter, the tracked catheter, and the secured catheter), in some embodiments, the SCIE can be mounted on multiple different catheters.

The MEA catheter can measure fields generated by the SCIE while determining the location of the catheter within the organ. The measured fields and determined locations are used to generate a field map assigning field measurements to each location in space. After the field mapping process is complete, the MEA catheter can be removed from the organ.

Figure 8:
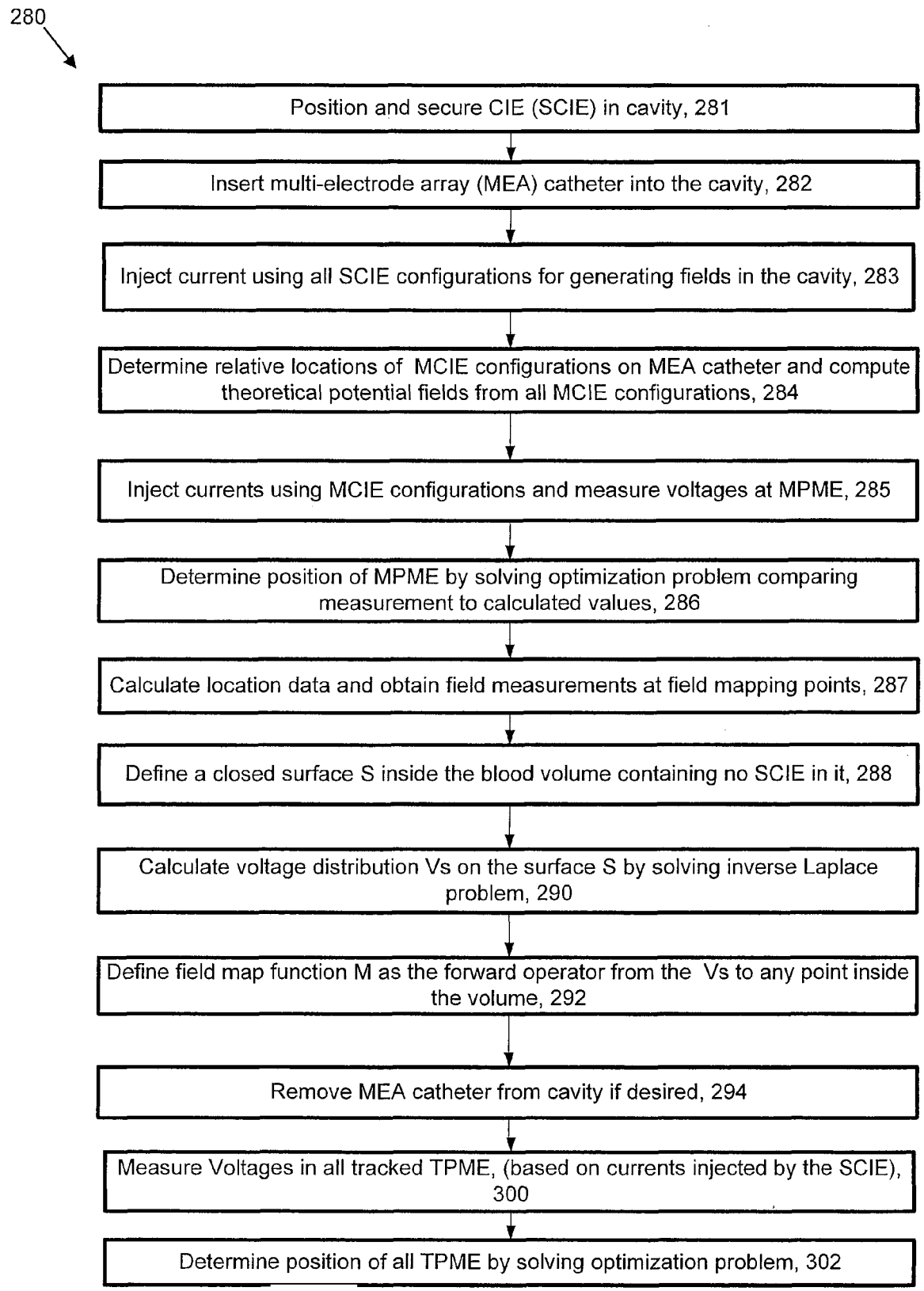
FIG. 8 is a flow diagram of an exemplary embodiment for generating a field map and using the field map to determine the positions of PME.

The tracked catheter that includes the TPME (a catheter other than the MEA catheter) is placed within the cardiac chamber and can move relative to the cardiac chamber. The TPME is able to measure the fields generated by the SCIE. The catheter can be tracked using the field map available for the chamber in which the catheter is positioned. Using the field map it is possible to determine the location of such potential measuring electrodes (TPME) that can measure the generated fields inside the volume covered by the field map. The position of a tracked TPME is determined by comparing the measured field value and the modeled field values. The position in the field map that holds a value matching the measurement of the tracked TPME is assigned as the location of that PME Referring to FIG. 8, in some examples, an MEA catheter can be used to generate a field map which is subsequently used to track the locations of other electrodes within the organ. Process 280 describes a method for determining the position of TPME within an organ using a field map generated using an MEA catheter in which the MEA catheter can be removed prior to tracking the location of the TPME. In step 281, current injecting electrodes are positioned in a fixed location in the cavity (the electrodes positioned in the fixed locations are referred to in this example as SCIE). The SCIE are used both for providing the signals used in generating the field map and for providing the signals used in tracking the locations of TPME using the field map. In step 282, a multi-electrode array catheter (MEA) that includes both the MCIE and MPME is inserted into the cavity. The relative locations of the MCIE and MPME on the MEA are known. In some embodiments, the electrodes of the MEA catheter are bundled into a compact configuration that enables the MEA catheter to be delivered to the heart chamber with minimal obstruction. Once inside the heart chamber, the electrodes of the catheter are deployed into a specified electrode arrangement relative to the MEA catheter (e.g., to provide known relative locations of the MCIE and MPME). In order to span the space 3 (or more) separate known configurations of MCIE need to inject current. In step 283, current is injected using the SCIE. In step 284, the system determines the relative locations of the MCIE configurations on the MEA catheter and computes theoretical potential fields from the MCIE configurations. In step 285, the MCIE inject current using different MCIE configurations. The 3 pairs of MCIE on the MEA catheter inject the current sequentially, one pair at a time, so that it is possible to trace the source of the measured MPME signals to a specific pair. In response to current flow between the pair of selected source/sink electrodes, the MPMEs distributed at multiple locations on the MEA catheter measure the resultant potential field present at the those multiple locations. The measured potentials are recorded. In step 286, the tracking of the electrodes on the MEA catheter is performed by solving an optimization problem that compares the measurement collected by MPME as a result of activation of the pairs of MCIE, to expected computed measurements in a given location. The location that minimizes the difference between the computed and measured potentials is assigned as electrode location.

In step 287, location data and field measurements are collected at multiple field mapping points within the cavity. The location data is determined using the fields generated by the MCIE and the field measurements are determined using the fields generated by the SCIE. In step 288 a closed surface, S, inside the volume and not including the SCIE is generated. In step 290, the voltage distribution on the surface is calculated. Using the calculated voltage distribution, in step 292, a field map is defined as the forward operator from the surface to any point inside the volume enclosed by the surface. Once a sufficient field map is generated, in step 294, the MEA catheter can be taken out of the body. This is advantageous when it is desired to have fewer catheters inside the body organ for clinical reasons, or when certain tracking fields interfere with other fields In step 300, the voltages on the tracked TPME are measured. In step 302, the position of the TPME is determined by solving an optimization problem using the previously generated field map.

Representative System

Figure 9:
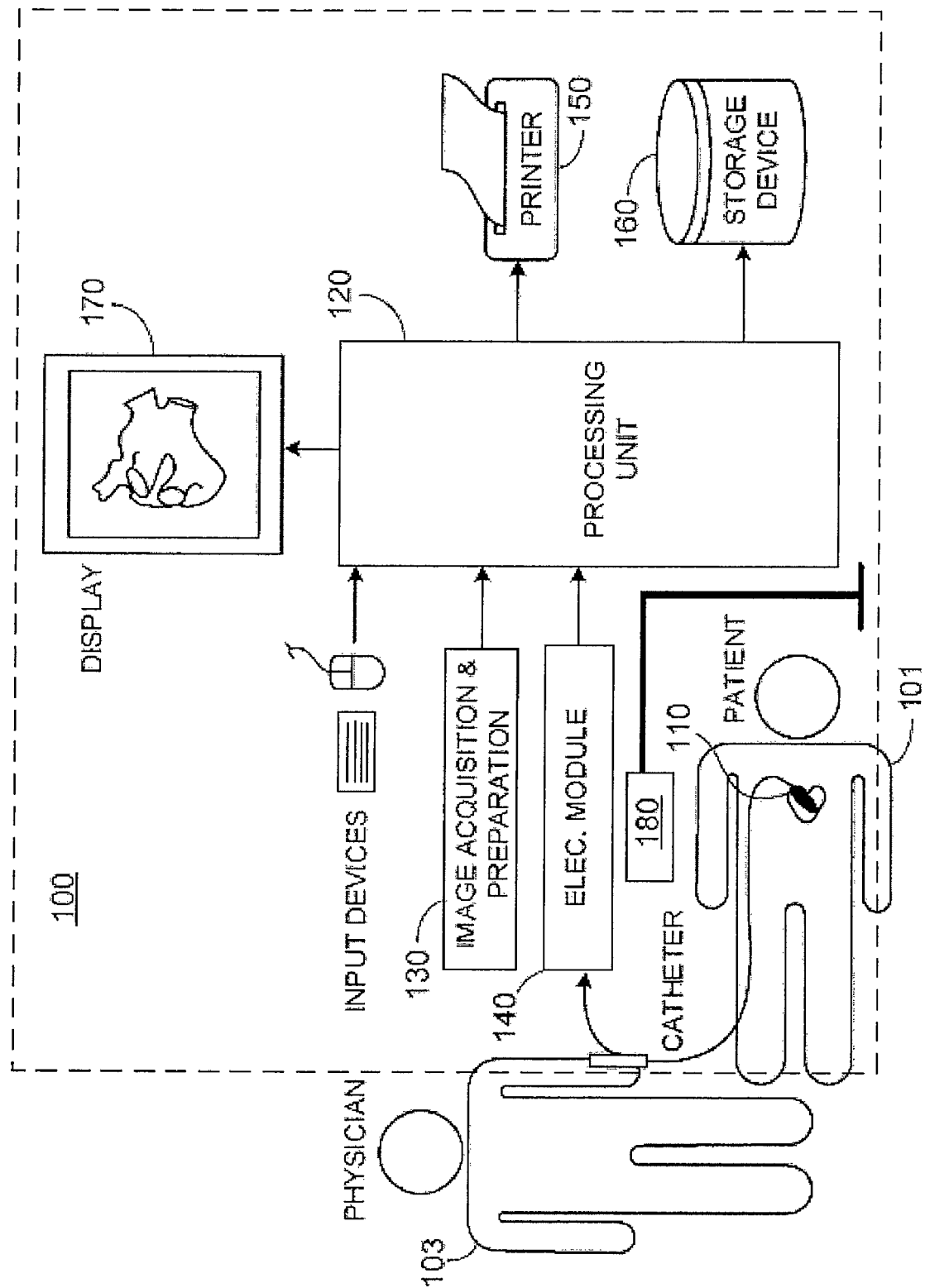
FIG. 9 is a schematic diagram of an exemplary system.

FIG. 9 shows a schematic diagram of an exemplary embodiment of a system 100 to facilitate the tracking of a catheter 110 (or multiple catheters) inside the heart cavity of a patient 101 using the pre-determined model of the field as described above. The catheter 110 is a moveable catheter 110 having multiple spatially distributed electrodes. The catheter(s) are used by a physician 103 to perform various medical procedures, including cardiac mapping and/or treatments such as ablation. More particularly, the catheter(s) can be tracked based on measurements of fields by the electrodes using a pre-determined model of the field such as a field map that provides expected signal measurements of the field at various locations within the heart cavity.

System 100 includes an electronics module 140 coupled to processing unit 120 for controlling the electrodes on catheter 110 and the CIE in the fixed locations, including a signal generation module for injecting current into the heart cavity through the CIEs and a signal acquisition module for measuring potentials through the PMEs. The electronics module 140 can be implemented using analog or digital electronics, or a combination of both. Such exemplary configurations, which are intended to be non-limiting, are now described.

Figure 10:
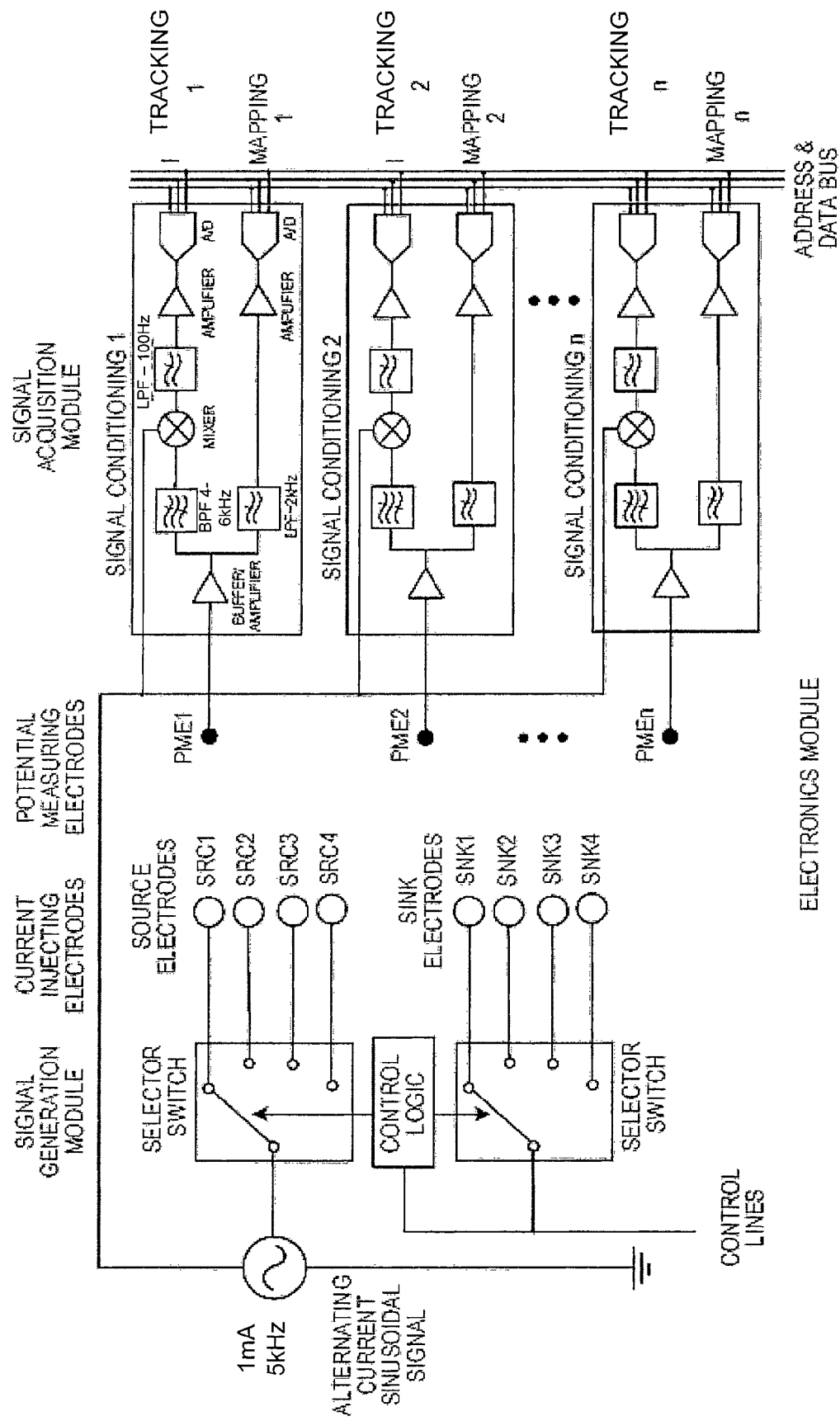
FIG. 10 is a schematic diagram of an analog implementation of a signal generation module (SGM) and signal acquisition module (SAM) for an electronics module coupled current emitting electrodes and potential measuring electrodes.

Referring to FIG. 10, the signal generation and acquisition modules are implemented using analog hardware. The signal generation module (SGM) depicted supports 8 CIEs defining 4 source/sink electrode pairs, where SRC refers to a source electrode and SNK refers to a sink electrode. It should be appreciated that other configurations of CIE are possible. Examples of such a configuration could be quadruples involving 4 CIE, or non-symmetrical configurations involving 3 CIE. For simplicity the method using electrode pairs will be explained, but the same method can be applied using other configurations. In general, at least 3 separate configurations of CIE are used in order to span the 3D space and provide XYZ coordinates of other electrodes. For the purpose of this example, each pair is driven using a 5 kHz oscillating 1 mA current source. Other driving frequencies, for example, 10 kHz, can be used. A selector switch is used to select each of the pairs sequentially based on control signals provided by the processing unit or other control logic. Each channel in the signal generation module is connected to a current injecting electrode. In this case the source and sink electrodes are pre-selected permanently such that each electrode is always either a source or a sink, although this need not be the case in other embodiments The signal acquisition module (SAM) buffers and amplifies the signals as they are collected by the potential measuring electrodes. The buffer prevents the acquisition system from loading the signals collected by the electrodes. After buffering and amplification, the signals are split and filtered into two channels, one for detecting the tracking signal (i.e., the signals produced in response to the CIEs) and one for detecting the signal generated by the heart's electrical activation (i.e., cardiac mapping). Because the heart's electrical activity (e.g., the cardiac signals) is primarily below 2 kHz, a low pass filter (LPF) is used to separate the cardiac mapping potential signals from those produced in response to the CIEs. The low pass filter may be implemented as an active filter responsible for both filtering and amplification. The signal is then sampled by an analog to digital converter. To support bandwidth and resolution requirements the converter may sample at >4 kHz at 15 bits per sample. After sampling, the signals are passed to the processing unit for further analysis. Both the LPF and A/D may be configured such that the filter and sample frequency can be changed by software control (not drawn).

The second channel following the input buffer detects the tracking signal (e.g., the signals measured in response to current injected by the CIE). In this embodiment, the detection is implemented using a lock-in amplifier approach to detect amplitude. It should be appreciated that other implementation can be used to accomplish the same task. In this channel the signal is first filtered using a band pass filter (BPF) whose pass band frequency is centered on the 5 kHz generated by the SGM. Following the BPF, the signal is multiplied by the same 5 kHz signal generated by the SGM using a mixer. As a result, the signal is down converted to DC such that its value following the down conversion is proportional to its amplitude before the down-conversion. The signal is then filtered using a very narrow LPF of roughly 100 Hz. The filter bandwidth has two effects. On the one hand, the narrower the filter the better noise performance will be. On the other hand, the wider the filter, the more tracking updates are available per second. A filter setting of 100 Hz provides excellent noise performance. After filtering, the signal is amplified and sampled by an analog to digital converter. The converter in this case may sample at 200 Hz using 15 bits per sample. After sampling, the signals are passed to the processing unit for further analysis. As before, the channel properties can be configured to be changed by software control (not drawn).

While the embodiment described above in relation to FIG. 10 described an analog signal generation and acquisition modules, in some examples a digital implementation can be used. For example, referring to FIG. 11, the signal generation and acquisition modules have a digital implementation. The SGM generates the required signals using an array of n digital to analog converters (D/A). In a preferred embodiment n=8. In another preferred embodiment, n=6. It should be appreciated that instead of n D/As it is possible to use fewer D/As and a multiplexed sample and hold amplifier. The signals generated by the D/As are controlled and timed by the processing unit. In one embodiment, the signals may mimic those described in the analog implementation whereby a sinusoidal signal is switched between electrodes. In other embodiments, however, the digital implementation provides more flexibility in that more complex signals (e.g., different frequencies, simultaneous activation of multiple electrodes) may be driven. After the conversion to an analog signal, the signals are buffered by an amplifier capable of driving the necessary current (<2 mA) at relevant frequencies (<30 kHz). After buffering, a processor controlled switch is used to support a high impedance mode. This is necessary in order to block a particular electrode from acting as a source or a sink at a particular time.

Figure 11:
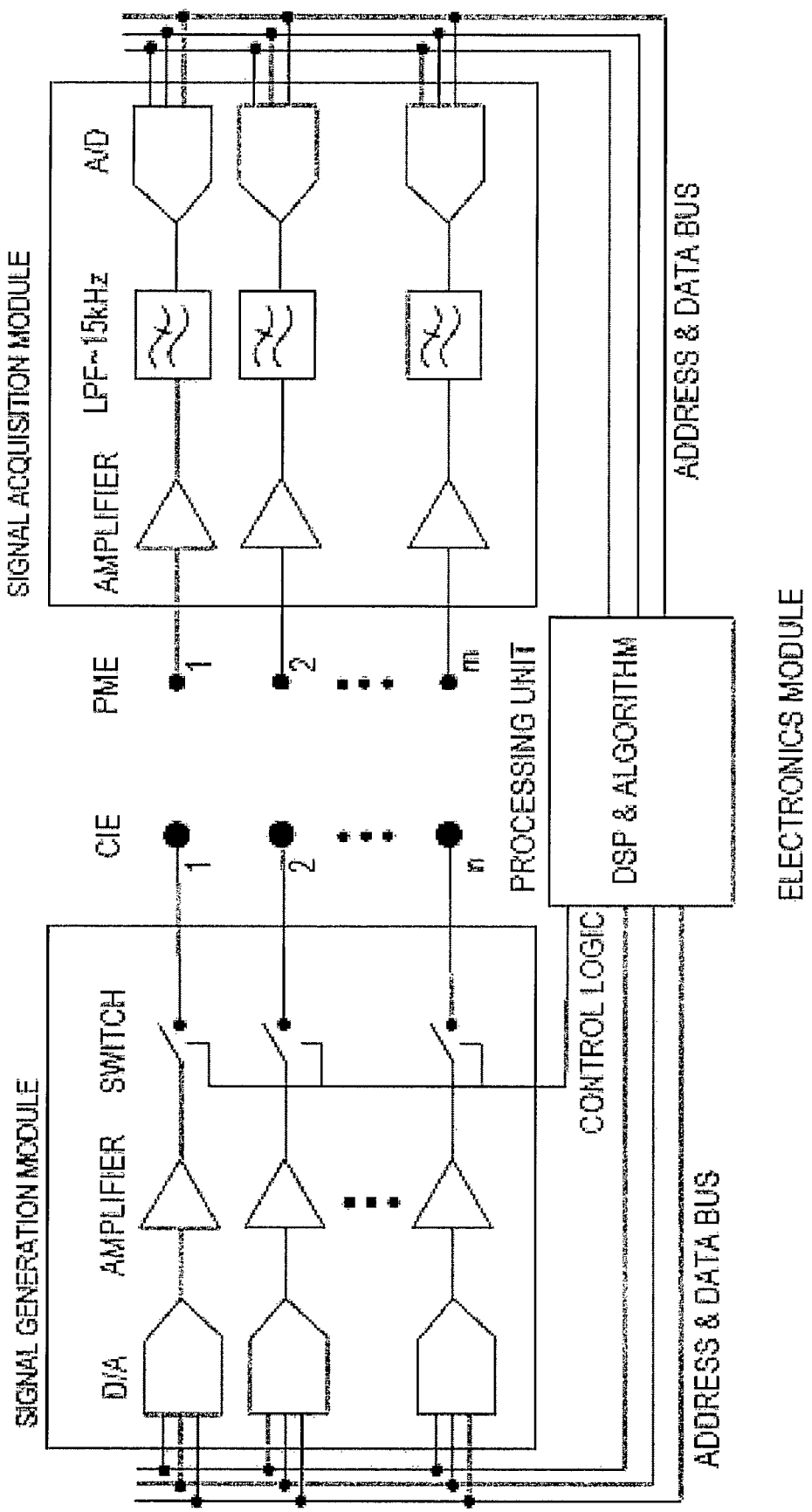
FIG. 11 is a schematic diagram of a digital implementation of a signal generation module (SGM) and signal acquisition module (SAM) for an electronics module coupled to current emitting electrodes and potential measuring electrodes.

In the SAM hardware, an input stage amplifies and buffers the signal. Following amplification the signal is low pass filtered in a wide enough band such that both the heart's electrical activity (<2 kHz) and signals generated by the SGM are kept inside the filtered band. In FIG. 11 the frequency band is 15 kHz. Following the filter, the signal is sampled above Nyquist frequency (>30 kHz) at 15 bits per sample. The sampled signals are then transferred to the processing unit which uses digital signal processing (DSP) techniques to filter the two channels in each electrode and down-convert the tracking signal appropriately.

A relatively small number of CIEs can result in a relatively large number of possible electrode pair combinations that can be activated to enable different potential field configurations to be formed inside the heart cavity, in which the catheter 110 is deployed and thus enhance the robustness of the tracking procedure. For example, six (6) electrodes can be paired into fifteen (15) combinations of different source/sink pairs, thus resulting in fifteen different potential fields, for a particular potential value, formed inside the medium. As noted above, to achieve high robustness of the tracking procedure, the various source/sink electrodes may be mounted at different locations in the organ or relative to the organ.

Preferably, the current injecting electrodes are designed to have low impedance at the interface between electrode and blood. The impedance between electrodes and blood is determined by the surface area of the electrode and electrode material. The larger the surface area, the lower the impedance In some embodiments, a larger surface area for CIEs is preferred in order to reduce their impedance at the interface to blood and allow the injection of current. In some embodiments, specialized coatings such as Platinum Black, Iridium Oxide and Titanium Nitride may be applied to one or more of the CIEs, one or more of the PMEs, or all of the catheter electrodes to reduce impedance of electrodes for a given surface area.

In yet further embodiments, one or more of the electrodes can be driven to function as both a CIE and a PME. For example, when it is desired to use an electrode as both PME and CIE, the electrode is connected to both a signal acquisition module and a signal generation module. For example, when the electrode is not used as a CIE to drive a current, the switch in the signal generation module corresponding to the respective electrode is opened. Accordingly, time division multiplexing schemes in the driving electronics of module can be used to operate a given catheter electrode as either a CIE or a PME. In yet another example, the electronics module can drive a given electrode so that it functions as a CIE at high frequencies and a PME at low frequencies (such as might be useful for cardiac mapping.)

As noted above, the PMEs on catheter 110 can also used for cardiac mapping, such as that described in commonly owned patent application Ser. No. 11/451,898, entitled "NON-CONTACT CARDIAC MAPPING, INCLUDING MOVING CATHETER AND MULTI-BEAT INTEGRATION" and filed Jun. 13, 2006, the contents of which are incorporated herein by reference. As also noted above, because the frequency of the current injected by CIEs (e.g., 5 kHz) is much higher than the frequency of the electrical activity of the patient's heart (e.g., the frequency of the cardiac signals), the signal acquisition module can separate signals measured by the PMEs based on frequency to distinguish tracking signals measured in response to currents injected by the CIE from cardiac mapping signals (e.g., frequencies higher than 2 kHz, and lower than 2 kHz, respectively.) Furthermore, in additional embodiments, catheter 110 may include separate electrodes used only for cardiac mapping.

The system 100 further includes the processing unit 120 which performs several of the operations pertaining to the tracking procedure, including the determination of catheter electrode locations that result in the best fit between the measured signals and those calculated for different positions of the catheter. Additionally, the processing unit 120 can subsequently also perform the cardiac mapping procedure, including a reconstruction procedure to determine the physiological information at the endocardium surface from measured signals, and may also perform post-processing operations on the reconstructed physiological information to extract and display useful features of the information to the operator of the system 100 and/or other persons (e.g., a physician). For example, the system 100 can display the location of the catheter(s) relative to a surface of the heart. In some embodiments, a stabilized representation of the heart and position can be used to display the position of the catheter as the shape of the heart changes during the heart's cycle.

The signals acquired by the various electrodes of catheter 110 during the tracking and/or the mapping procedure are passed to the processing unit 120 via electronics module 140. As described above, electronics module 140 can be used to amplify, filter and continuously sample intracardiac potentials measured by each electrode.

In some embodiments, the electronics module 140 is implemented by use of integrated components on a dedicated printed circuit board. In other embodiments, some of the signal conditioning tasks may be implemented on a CPU, FPGA or DSP after sampling. To accommodate safety regulations, the signal conditioning module is isolated from high voltage power supplies. The electronics module is also protected from defibrillation shock, and interference caused by nearby pacing or ablation.

The processing unit 120 shown in FIG. 9 is a processor-based device that includes a computer and/or other types of processor-based devices suitable for multiple applications. Such devices can include volatile and non-volatile memory elements, and peripheral devices to enable input/output functionality. Such peripheral devices include, for example, a CD-ROM drive and/or floppy drive, or a network connection, for downloading related content to the connected system. Such peripheral devices may also be used for downloading software containing computer instructions to enable general operation of the respective unit/module, and for downloading software implemented programs to perform operations in the manner that will be described in more detailed below with respect to the various systems and devices shown in FIG. 9. Alternatively, the various units/modules may be implemented on a single or multi processor-based platform capable of performing the functions of these units/modules. Additionally or alternatively, one or more of the procedures performed by the processing unit 120 and/or electronics module 140 may be implemented using processing hardware such as digital signal processors (DSP), field programmable gate arrays (FPGA), mixed-signal integrated circuits, ASICS, etc. The electronics module 140 is typically implemented using analog hardware augmented with signal processing capabilities provided by DSP, CPU and FPGA devices.

As additionally shown in FIG. 9, the system 100 includes peripheral devices such as printer 150 and/or display device 170, both of which are interconnected to the processing unit 120. Additionally, the system 100 includes storage device 160 that is used to store data acquired by the various interconnected modules, including the volumetric images, raw data measured by electrodes and the resultant endocardium representation computed there from, the reconstructed physiological information corresponding to the endocardium surface, etc.

Other Embodiments

While in at least some of the embodiments described above, the CIE pairs are shown as positioned in the coronary sinus, other locations could be used to secure the CIE pairs. For example, the CIE pairs could be secured in the, atrial appendage, apex, and the like. Additionally, in some embodiments, the CIE pairs could be positioned outside of the patient's body (e.g., affixed to the surface of the patient's chest). In some additional embodiments, the CIE pairs could be positioned within the organ itself, e.g., within the heart chamber.

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

Accordingly, other embodiments are within the scope of the following claims.

What is claimed is:

1. A method comprising:
   securing multiple sets of current injecting electrodes to one or more stable locations relative to an organ in a patient's body;
   causing current to flow among the multiple sets of current injecting electrodes to generate a field in the organ;
   in response to current flow caused by the multiple sets of current injecting electrodes, measuring the field at each of one or more additional electrodes,
   determining expected signal measurements of the field inside the organ using a previously determined model of the field; and
   determining a position of each of the one or more additional electrodes in the organ based on the measurements made by the additional electrodes and the determined expected signal measurements of the field;
   wherein determining the position of the one or more additional electrodes in the organ based on measurements made by the additional electrodes and the determined expected signal measurements of the field comprises solving an optimization problem that minimizes a collective difference between each of the measured signals and an estimate for each of the respective measured signals as a function of the position of the measurement.

2. The method of claim 1, wherein the estimate for each of the respective measured signals comprises a differentiable function.

3. The method of claim 1, wherein the one or more additional electrodes comprise one or more electrodes used for delivering ablation energy for ablating tissue of the organ.

4. The method of claim 1, wherein the one or more additional electrodes comprise one or more electrodes used for measuring the electrical activity of the organ.

5. The method of claim 1, further comprising generating the previously determined model of the field.

6. The method of claim 5, wherein generating the previously determined model of the field comprises:
   causing current to flow among the multiple sets of current injecting electrodes to generate a field in the organ;
   obtaining the positions of one or more measuring electrodes;
   in response to the current flow, measuring the field at multiple locations in the organ using the one or more measuring electrodes; and
   modeling the field using the measurements of the field measured by the one or more measuring electrodes and the positions of the one or more measuring electrodes.

7. The method of claim 6, wherein modeling the field comprises modeling the field based on physical characteristics.

8. The method of claim 7, wherein modeling the field based on physical characteristics comprises using Laplace's equation.

9. The method of claim 7, wherein modeling the field based on physical characteristics comprises using Poisson's equation.

10. The method of claim 7, wherein modeling the field based on physical characteristics comprises modeling a homogeneous medium.

11. The method of claim 7, wherein modeling the field based on physical characteristics comprises modeling an inhomogeneous medium.

12. The method of claim 6, wherein modeling of the field further comprises representing the model using a function that correlates field measurements with position coordinates.

13. The method of claim 1, wherein the previously determined model of the field comprises a field map.

14. The method of claim 13, wherein the field map is a function that correlates the expected signal measurements with position coordinates within the organ.

15. The method of claim 14, wherein the function is a differentiable function.

16. The method of claim 1, wherein measuring the field comprises measuring potentials.

17. The method of claim 1, wherein the current-injecting electrodes operate at a frequency different from the frequency of normal electrical activity in the organ.

18. The method of claim 1, wherein the organ is a patient's heart.

19. The method of claim 1, wherein the one or more additional electrodes comprise one or more measuring electrodes configured to measure a current in response to current flow caused by the multiple sets of current injecting electrodes.

20. The method of claim 1, wherein the multiple sets of current injecting electrodes comprise multiple sets of current injecting electrodes mounted on one or more catheters that are placed inside the body and securing the current injecting electrodes to one or more stable locations relative an organ in a patient's body comprises securing the multiple sets of current injecting electrodes to an organ in the patient's body.

21. The method of claim 1, wherein the current injecting electrodes comprise one or more body-surface electrodes and securing the current injecting electrodes to one or more stable locations relative an organ in a patient's body comprises securing the current injecting electrodes to the patient's skin.

22. The method of claim 1, wherein the current injecting electrodes comprise both electrodes mounted on one or more catheters that are placed inside the body and body-surface electrodes.

23. A system comprising:
  multiple sets of current injecting electrodes configured to he secured to one or more stable locations relative to an organ in a patient's body;
  one or more additional electrodes configured to be positioned within the organ in the patient's body;
  an electronic control system coupled to the multiple sets of current injecting electrodes and the one or more additional electrodes, the electronic control system being configured to:
    cause current to flow among the multiple sets of current injecting electrodes to generate a field in the organ;
    in response to current flow caused by the multiple sets of current injecting electrodes, measure the field at each of one or more additional electrodes,
  a processing system coupled to the electronic system and configured to:
    determine expected signal measurements of the field inside the organ using a previously determined model of the field; and
    determine a position of each of the one or more additional electrodes in the organ based on the measurements made by the additional electrodes and the determined expected signal measurements of the field;
  wherein the processing system is configured to solve an optimization problem that minimizes a collective difference between each of the measured signals and an estimate for each of the respective measured signals as a function of the position of the measurement.

24. The system of claim 23, wherein the one or more additional electrodes comprise one or more electrodes used for delivering ablation energy for ablating tissue of the organ.

25. The system of claim 23, wherein the one or more additional electrodes comprise one or more electrodes used for measuring the electrical activity of the organ.

26. The system of claim 23, wherein the processing system is further configured to generate the previously determined model of the field.

27. A method comprising:
  securing at least three sets of current injecting electrodes to one or more stable locations relative to an organ in a patient's body;
  causing current to flow among the at least three sets of current injecting electrodes to generate a field in the organ:
  using a multi-electrode array located on a multi-electrode array catheter in the organ for tracking a position of the multi-electrode array catheter relative to the current injecting electrodes;
  measuring the field generated by the current injecting electrodes in multiple locations in the organ using the multi-electrode array;
  modeling the field using the measurements and the positions;
  determining expected signal measurements of the field at additional locations within the organ based on the model of the field; and
  determining a position of one or more additional electrodes in the organ relative to the current injecting electrodes based on measurements made by the additional electrodes and the determined expected signal measurements of the field:
  wherein the measuring of the field at the multiple locations comprises moving a catheter having one or more measuring electrodes to multiple locations within the organ, and using the measuring electrodes to measure the field for each of the multiple locations of the catheter: and
  wherein the additional locations correspond to regions inside the organ not interrogated by the movement of the catheter.

28. The method of claim 27, further comprising removing the multi-electrode array catheter from the organ prior to determining the position of one or more additional electrodes in the organ.

29. The method of claim 27, wherein the one or more additional electrodes comprise one or more electrodes mounted on one of more additional catheters.

30. The method of claim 27, wherein the one or more additional electrodes comprise one or more electrodes of the multi-electrode array.

31. The method of claim 27, wherein modeling the field comprises using Laplace's equation.

32. The method of claim 27, wherein modeling the field comprises modeling the field based on physical characteristics.

33. The method of claim 32, wherein modeling the field based on physical characteristics comprises using Poisson's equation.

34. The method of claim 32, wherein modeling the field based on physical characteristics comprises modeling a homogeneous medium.

35. The method of claim 32, wherein modeling the field based on physical characteristics comprises modeling an inhomogeneous medium.

36. The method of claim 32, wherein modeling of the field further comprises representing the model using a function that correlates field measurements with position coordinates.

37. The method of claim 27, wherein the additional locations within the organ comprise positions within the organ where the field was not measured.

38. The method of claim 37, wherein the positions within the organ where field was not measured comprise positions that are more than 5 mm away from positions where the field was measured.

39. The method of claim 37, wherein the positions within the organ where field was not measured comprise positions that are not lying between positions where the field was measured.

40. The method of claim 39, wherein determining a position of one or more additional electrodes in the field based on measurements made by the additional electrodes and the determined expected signal measurements of the field comprises solving an optimization problem that minimizes collective difference between each of the measured signals and an estimate for each of the respective measured signals as a function of the position of the measurement.

41. The method of claim 27, wherein determinine expected signal measurements comprises determining expected signal measurements using a non-interpolation based calculation.

42. The method of claim 27, wherein the multiple sets of current-injecting electrodes comprise at least three sets of current injecting electrodes, and wherein the causing of the current flow comprises causing current to flow between each set of current injecting electrodes, and wherein the field measured in response to the current flow comprise a field measurement for each set of the current injecting electrodes for each of the multiple positions.

43. The method of claim 27, wherein modeling the field comprises generating a field map.

44. The method of claim 27, further comprising displaying the determined location of the measuring electrode relative to a surface of the organ.

45. A system comprising:
at least three sets of current injecting electrodes configured to be secured to stable locations relative to an organ in a patient's body;
a multi-electrode array catheter comprising a multi-electrode array configured to be inserted in the organ for tracking a position of the multi-electrode array catheter relative to the current injecting electrodes;
one or more additional electrodes configured to be inserted in the organ;
an electronic control system coupled to the at least three sets of current injecting electrodes, to the multi-electrode array catheter, and to the one or more additional electrodes, the electronic control system being configured to:
cause current to flow among the multiple sets of current injecting electrodes to generate a field in the organ;
measure the field generated by the current injecting electrodes in multiple locations in the organ using the multi-electrode array;
a processing system coupled to the electronic system and configured to:
model the field using the measurements and the positions;
determine expected signal measurements of the field at additional locations within the organ based on the model of the field, the additional locations corresponding to regions inside the organ not interrogated by the movement of the catheter; and
determine a position of the one or more additional electrodes in the organ relative to the current injecting electrodes based on measurements made by the additional electrodes and the determined expected signal measurements of the field.

46. The system of claim 45, wherein the one or more additional electrodes comprise one or more electrodes mounted on one of more additional catheters.

47. The system of claim 45, wherein the one or more additional electrodes comprise one or more electrodes of the multi-electrode array.

48. The system of claim 45, wherein the multiple sets of current-injecting electrodes comprise at least three sets of current injecting electrodes.

49. A method comprising:
securing multiple sets of current injecting electrodes to a patient's body;
causing current to flow among the multiple sets of current injecting electrodes to generate a field in an organ in the patient's body;
in response to current flow caused by the multiple sets of current injecting electrodes, measuring the field at each of one or more additional electrodes,
determining expected signal measurements Of the field inside the organ using a previously determined model of the field; and
determining a position of each of the one or more additional electrodes in the organ based on the measurements made by the additional electrodes and the determined expected signal measurements of the field.

50. The method of claim 49, wherein determining the position of the one or more additional electrodes in the organ based on measurements made by the additional electrodes and the determined expected signal measurements of the field comprises solving an optimization problem that minimizes a collective difference between each of the measured signals and an estimate for each of the respective measured signals as a function of the position of the measurement.

51. A method comprising:
securing at least three sets of current injecting electrodes to one or more stable locations relative to an organ in a patient's body;
causing current to flow among the multiple sets of current injecting electrodes to generate a field in the organ;
using a multi-electrode array located on a multi-electrode array catheter in the organ for tracking a position of the multi-electrode array catheter relative to the current injecting electrodes;
measuring the field generated by the current injecting electrodes in multiple locations in the organ using the multi-electrode array;
modeling the field using the measurements and the positions;
determining expected signal measurements of the field at additional locations within the organ based on the model of the field; and
determining a position of one or more additional electrodes in the organ relative to the current injecting electrodes based on measurements made by the additional electrodes and the determined expected signal measurements of the field;
wherein modeling of the field further comprises representing the model using a function that correlates field measurements with position coordinates.

52. The method of claim 51, further comprising removing multi-electrode array catheter from the organ prior to determining the position of one or more additional electrodes in the organ.

53. The method of claim 51, wherein the one or more additional electrodes comprise one or more electrodes mounted on one of more additional catheters.

54. The method of claim 51, wherein modeling the field based on physical characteristics comprises using Laplace's equation.

55. The method of claim 51, wherein modeling the field comprises modeling the field based on physical characteristics.

56. The method of claim 55, wherein modeling the field based on physical characteristics comprises using Poisson's equation.

57. The method of claim 55, wherein modeling the field based on physical characteristics comprises modeling a homogeneous medium.

58. The method of claim 55, wherein modeling the field based on physical characteristics comprises modeling an inhomogeneous medium.

59. The method of claim 55, wherein modeling of the field further comprises representing the model using a function that correlates field measurements with position coordinates.

60. The method of claim 51, wherein the additional locations within the organ comprise. positions within the organ where the field was not measured.

61. The method of claim 60, wherein the positions within the organ where field was not measured comprise positions that are more than 5 mm away from positions where the field was measured.

62. The method of claim 60, wherein the positions within the organ where field was not measured comprise positions that are not lying between positions where the field was measured.

63. The method of claim 62, wherein determining a position of one or more additional electrodes in the field based on measurements made by the additional electrodes and the determined expected signal measurements of the field comprises solving an optimization problem that minimizes collective difference between each of the measured signals and an estimate for each of the respective measured signals as a function of the position of the measurement.

64. The method of claim 51, wherein the multiple sets of current-injecting electrodes comprise at least three sets of current injecting electrodes, and wherein the causing of the current flow comprises causing current to flow between each set of current injecting electrodes, and wherein the field measured in response to the current flow comprise a field measurement for each set of the current injecting electrodes for each of the multiple positions.

65. The method of claim 51, wherein modeling the field comprises generating a field map.

66. The method of claim 51, further comprising displaying the determined location of the measuring electrode relative to a surface of the organ.

67. A method comprising:
 securing at least three sets of current injecting electrodes to one or more stable locations relative to an organ in a patient's body;
 causing current to flow among the multiple sets of current injecting electrodes to generate a field in the organ;
 using a multi-electrode array located on a multi-electrode array catheter in the organ for tracking a position of the multi-electrode array catheter relative to the current injecting electrodes:
 measuring the field generated by the current injecting electrodes in multiple locations in the organ using the multi-electrode array;
 modeling the field using the measurements and the positions;
 determining expected signal measurements of the field at additional locations within the organ based on the model of the field; and
 determining a position of one or more additional electrodes in the organ relative to the current injecting electrodes based on measurements made by the additional electrodes and the determined expected signal measurements of the field;
 wherein the additional locations within the organ comprise positions within the organ where the field was not measured; and
 wherein the positions within the organ where field was not measured comprise positions that are more than 5 mm away from positions where the field was measured.

68. A method comprising:
 securing at least three sets of current injecting electrodes to one or more stable locations relative to an organ in a patient's body;
 causing current to flow among the multiple sets of current injecting electrodes to generate a field in the organ:
 using a multi-electrode array located on a multi-electrode array catheter in the organ for tracking a position of the multi-electrode array catheter relative to the current injecting electrodes;
 measuring the field generated by the current injecting electrodes in multiple locations in the organ using the multi-electrode array;
 modeling the field using the measurements and the positions;
 determining expected signal measurements of the field at additional locations within the organ based on the model of the field; and
 determining a position of one or more additional electrodes in the organ relative to the current injecting electrodes based on measurements made by the additional electrodes and the determined expected signal measurements of the field;
 wherein the additional locations within the organ comprise positions within the organ where the field was not measured; and
 wherein the positions within the organ where field was not measured comprise positions that are not lying between positions where the field was measured.

69. A method comprising:
 securing at least three sets of current injecting electrodes to one or more stable locations relative to an organ in a patient's body;
 causing current to flow among the multiple sets of current injecting electrodes to generate a field in the organ;
 using a multi-electrode array located on a multi-electrode array catheter in the organ for tracking a position of the multi-electrode array catheter relative to the current injecting electrodes;
 measuring the field generated by the current injecting electrodes in multiple locations in the organ using the multi-electrode array;
 modeling the field using the measurements and the positions;
 determining expected signal measurements of the field at additional locations within the organ based on the model of the field; and
 determining a position of one or more additional electrodes in the organ relative to the current injecting electrodes based on measurements made by the additional electrodes and the determined expected signal measurements of the field; and
 wherein determining expected signal measurements comprises determining expected signal measurements using, a non-interpolation based calculation.

* * * * *

UNITED STATES PATENT AND TRADEMARK OFFICE
CERTIFICATE OF CORRECTION

PATENT NO.      : 8,137,343 B2
APPLICATION NO. : 12/258677
DATED           : March 20, 2012
INVENTOR(S)     : Doron Harlev and Rotem Eldar It is certified that error appears in the above-identified patent and that said Letters Patent is hereby corrected as shown below:

Claim 20, Column 27, Line 3 - delete "an" and insert -- to an --, therefor.

Claim 21, Column 27, Line 9 - delete "an" and insert -- to an --, therefor.

Claim 23, Column 27, Line 17 - delete "he" and insert -- be --, therefor.

Claim 27, Column 27, Line 60 - delete "organ:" and insert -- organ; --, therefor.

Claim 27, Column 28, Line 10 - delete "field:" and insert -- field; --, therefor.

Claim 27, Column 28, Line 15 - delete "catheter:" and insert -- catheter; --, therefor.

Claim 29, Column 28, Line 25 - delete "one of more" and insert -- one or more --, therefor.

Claim 41, Column 28, Line 65 - delete "determinine" and insert -- determining --, therefor.

Claim 46, Column 29, Line 52 - delete "one of more" and insert -- one or more --, therefor.

Claim 49, Column 30, Line 1 - delete "Of" and insert -- of --, therefor.

Claim 53, Column 30, Line 49 - delete "one of more" and insert -- one or more --, therefor.

Claim 60, Column 31, line 2 - delete "comprise." and insert -- comprise --, therefor.

Claim 67, Column 31, Line 43 - delete "electrodes:" and insert -- electrodes; --, therefor.

Claim 68, Column 32, Line 8 (Approx.) - delete "organ:" and insert -- organ; --, therefor.

Claim 69, Column 32, Line 56 (Approx.) - delete "using," and insert -- using --, therefor.

Signed and Sealed this
Fifteenth Day of May, 2012

David J. Kappos
*Director of the United States Patent and Trademark Office*